United States Patent
Johnson et al.

(10) Patent No.: US 6,623,991 B2
(45) Date of Patent: Sep. 23, 2003

(54) METHOD OF MEASURING MESO-SCALE STRUCTURES ON WAFERS

(75) Inventors: Kenneth C. Johnson, Santa Clara, CA (US); Fred E. Stanke, Cupertino, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

(21) Appl. No.: 09/999,410

(22) Filed: Oct. 31, 2001

(65) Prior Publication Data

US 2002/0090743 A1 Jul. 11, 2002

Related U.S. Application Data

(63) Continuation of application No. 09/735,286, filed on Feb. 12, 2001, now Pat. No. 6,340,602.
(60) Provisional application No. 60/172,851, filed on Dec. 10, 1999, and provisional application No. 60/194,651, filed on Apr. 4, 2000.

(51) Int. Cl.$^7$ ............................................... H01L 21/00
(52) U.S. Cl. ............................................................ 438/7
(58) Field of Search ........................... 438/7, 5–6, 8–13, 438/14–19, 800, 795; 356/369, 152.2, 612, 445, 947

(56) References Cited

U.S. PATENT DOCUMENTS

| | | | |
|---|---|---|---|
| 4,053,232 A | * 10/1977 | Dill et al. | 250/225 |
| 4,757,207 A | 7/1988 | Chappelow et al. | 250/491.1 |
| 4,999,014 A | * 3/1991 | Gold et al. | 356/369 |
| 5,166,752 A | * 11/1992 | Spanier et al. | 250/201.2 |
| 5,293,216 A | * 3/1994 | Moslehi | 219/121.6 |
| 5,900,633 A | * 5/1999 | Solomon et al. | 250/339.08 |
| 6,100,985 A | * 8/2000 | Scheiner et al. | 250/341.1 |
| 6,281,027 B1 | 8/2001 | Wei et al. | 438/14 |
| 6,327,035 B1 | 12/2001 | Li et al. | 356/432 |

OTHER PUBLICATIONS

W. Kong et al., "A Hybrid Analysis of Ellipsometry Data from Patterned Structures," *American Institute of Physics*, 1–56396–967–X/01, Characterization and Metrology for ULSI Technology: 2000 International Conference, 2001, pp. 373–377.

M.E. Lee et al., "Analysis of Reflectometry and Ellipsometry Data from Patterned Structures," International Conference on Characterization and Metrology for ULSI Technology, Gaithersburg, MD, Mar. 23–27, 1998, *AIP Conference Proceedings* 449, pp. 331–335, 1998, pp. 1–5.

W. Kong et al., "Analysis of Time–Evolved Spectroscopic Ellipsometry Data from Patterned Structures for Etching Process Monitoring and Control," paper 19.2, SRC TECHCON, Las Vegas, Nevada, Sep. 9–11, 1998, 4 pages in length.

(List continued on next page.)

*Primary Examiner*—Craig Thompson
(74) *Attorney, Agent, or Firm*—Stallman & Pollock LLP

(57) ABSTRACT

A method of measuring at least one parameter associated with a portion of a sample having formed thereon one or more structures with at least two zones each having an associated zone reflectance property. The method includes the steps of illuminating the zones with broadband light, and measuring at least one reflectance property of light reflected from the at least two zones. The measurement includes a substantial portion of non-specularly scattered light, thereby increasing the quality of the measurement. The method further includes the step of fitting a parameterized model to the measured reflectance property. The parameterized model mixes the zone reflectance properties of the zones to account for partially coherent light interactions between the two zones.

12 Claims, 19 Drawing Sheets

OTHER PUBLICATIONS

P.A. Heimann, "Optical Etch–Rate Monitoring Using Active Device Areas: Lateral Interference Effects," *J. Electrochem. Soc.*, vol. 132, No. 8, Aug. 1985, pp. 2003–2006.

P.A. Heimann et al., "Optical Etch–Rate Monitoring: Computer Simulation of Reflectance," *J. Electrochem. Soc.*, vol. 131, No. 4, Apr. 1984, pp. 881–885.

H.L. Maynard et al., "Multiwavelength ellipsometry for real–time process control of the plasma etching of patterned samples," *J. Vac. Sci. Technol. B*, vol. 15, No. 1, Jan./Feb. 1997, pp. 109–115.

* cited by examiner

METHOD OF MEASURING MESO-SCALE STRUCTURES ON WAFERS

CROSS-REFERENCE TO RELATED APPLICATIONS

This application is a continuation of U.S. patent application Ser. No. 09/735,286 filed on Feb. 12, 2001, now U.S Pat. No. 6,340,602. This application also claims the benefit of U.S. Provisional Application No. 60/172,851, filed on Dec. 10, 1999, and No. 60/194,651, filed Apr. 4, 2000. Further, Application Ser. No. 09/735,286, now U.S. Pat. No. 6,340,602, Nos. 60/172,851 and 60/194,651 are incorporated herein in their entirety by reference.

FIELD OF THE INVENTION

The present invention pertains to processing wafers, and in particular to measuring parameters indicative of the quality of the wafer processing.

BACKGROUND OF THE INVENTION

Chemical-mechanical polishing (CMP) is a well-known process in the semiconductor industry used to remove and planarize layers of material deposited on a semiconductor device to achieve a planar topography on the surface of the semiconductor device. To remove and planarize the layers of the deposited material, including dielectric and metal materials, CMP typically involves wetting a pad with a chemical slurry containing abrasive components and mechanically polishing the front surface of the semiconductor device against the wetted pad to remove the layers of deposited materials on the front surface of the semiconductor device and planarize the surface.

FIG. 1 is a schematic view of a prior art CMP apparatus 10. CMP apparatus 10 includes a wafer carrier 11 for holding a semiconductor wafer 12 having a surface 12S to be polished. Wafer carrier 11 is mounted for continuous rotation about an axis A1 in a direction indicated by arrow 13 via a drive motor 14 operatively connected to the wafer carrier. Wafer carrier 11 is adapted so that a force indicated by arrow 15 is exerted on semiconductor wafer 12.

CMP apparatus 10 also includes a polishing platen 16 mounted for continuous rotation about an axis A2 in a direction indicated by arrow 17 by a drive motor 18 operatively connected to the polishing platen. A polishing pad 19, formed of a material such as blown polyurethane, is mounted to polishing platen 16. A polishing slurry containing an abrasive fluid, such as silica or alumina abrasive particles suspended in either a basic or an acidic solution, is dispensed onto polishing pad 19 through a conduit 20 arranged adjacent the polishing pad, from temperature controlled reservoir 21.

Wafer carrier 11 rotates in a direction indicated by arrow 13 about axis A1. Polishing platen 16 rotates in a direction indicated by arrow 17 about axis A2. The polishing slurry is dispensed onto polishing pad 19 through conduit 20, from temperature controlled reservoir 21 as the wafer carrier and polishing platen rotate about their respective axes. The force between the polishing platen and the wafer carrier and their relative rotation, in combination with the mechanical abrasion and chemical effects of the slurry, serve to polish wafer surface 12S.

FIG. 2 illustrates a semiconductor device prior to CMP. As shown, substrate 12 has a source region 112 and a drain region 114, and also includes lightly doped drains 116 and 118. Source and drain regions 112 and 114 are formed according to conventional processes, after formation of a gate oxide layer 122 and gate 124. Following formation of gate 124, a first inter-level dielectric (ILD) layer 120 is deposited over gate 124. First ILD layer is 120 formed of silicon dioxide, but may be formed of other dielectric materials.

After formation of first ILD layer 120, the layer is etched to form an opening that is filled with tungsten to form a contact plug 126, which provides ohmic contact to source region 112. Although not shown in the plane of the cross-section of FIG. 2, a similar contact plug is formed for drain region 114.

Thereafter, a first metal layer 128 is deposited on first ILD layer 120. First metal layer 128 is formed of a metal, such as copper, aluminum, or tungsten. A second ILD layer 130, an etch stop layer (not shown), and a third ILD layer 134 are then consecutively formed on the first metal layer 128. Layer 130, the etch stop layer and layer 134 are formed, patterned and etched according to conventional techniques to form openings, particularly via holes 136a and trenches 138a, via holes 136a being contiguous with respective trenches 138a. That is, each via hole shares a common, upper boundary at the interface between the via hole and the trench, where the via opens into the trench. According to the structure shown, a dual-inlaid process is used to deposit a second metal layer 139 simultaneously within via holes 136a and trenches 138a to form vias 136 and interconnects 138 (i.e., lines). The third ILD layer 134 includes fine pitch dielectric portions 134a separating interconnects 138 from each other. Second metal layer 139 may be copper, aluminum or tungsten. In each case, the metal is put down in layer form on the order of 3,000 to 11,000 angstroms in thickness.

Once the basic structure of FIG. 2 is in place, CMP is carried out using CMP apparatus 10 of FIG. 1 to remove that portion of metal layer 139 above trenches 138a such that the trenches 138a form separate interconnects 138, and the exposed surface of the semiconductor device is polished and planarized for subsequent deposition steps, such as higher-level metal interconnects. With reference now to FIG. 3A, it is preferred that metal layer 139 be removed by polishing such that dielectric portions 134a separate trenches 138, with upper surface 12S being planarized.

With reference now to FIG. 3B, it often occurs that some of the metal layer 139 is not entirely removed, leaving a "residue" 150 of material (here, a portion of metal layer 139). Generally, residue is any material that is supposed to have been removed from the surface of the wafer during processing. Residue generally occurs in a region that has not been polished sufficiently. Residue 150a lies over the narrow dielectric spaces of the structure, and residue 150b lies over the dielectric field.

The presence of residue 150 is problematic because it is not part of the planned semiconductor structure and thus will, in all likelihood, interfere with the performance of the resulting device. For example, in FIG. 3B, residue 150 short-circuits interconnects 138. Thus, the wafer shown in FIG. 3B would need to be re-polished, re-processed, or scrapped, unless the amount of residue was deemed minimal enough to allow the wafer to continue on to the next process.

Unfortunately, the most effective method presently available for determining if residue is present on a wafer appears to be visual inspection of the wafer surface after it has been polished. This is a time-consuming and labor-intensive process. Accordingly, it would be preferred to have an automated, time-saving way to assess the presence or absence of residue.

One approach to measuring residue is to treat the thin layer of typically metalic residue as a transparent film, and to measure its thickness as part of an homogenous film stack with an instrument like the KLA/Tencor UV1050, available from KLA/Tencor, Inc. This method is suitable for measuring residue 150b overlying a large area of field dielectric, but has a general requirement that constrains its utility. The region where the residue measurement is made must be laterally homogeneous, i.e., the stack must include only flat layers that are substantially uniform over the dimensions of the spot size of the instrument, down to the first opaque layer below the residue. This is a serious limitation since the process in question may leave residue over structures that are laterally heterogeneous over the spot size of the instrument.

For example, with reference to FIG. 4, residue 150a is in the vicinity of interconnects 138, which, in a modern integrated circuit, can have dimensions of 250 nm or less, whereas optical instruments typically have a measurement spot-size of several microns or tens of microns. Since these features are smaller than the wavelength of light, it is not possible to focus between the features, making this method unsuitable for measuring such residue.

With reference now to FIG. 5, it often occurs that some regions polish faster than others causing erosion 160 and dishing 162. In the example shown, the polish process was designed to remove metal 139 (FIG. 2), and so removes dielectric 134 more slowly. As a result, after the polishing reaches the top of dielectric 134 the metal polishes faster than the dielectric. Generally some degree of overpolish is necessary to insure that there is no residue, as discussed above. In an array area, the rapid polishing of the metal causes dishing 162 of metal lines 138 with respect to dielectric spaces 134a, and erosion 160 of dielectric lines 134a with respect to the neighboring field dielectric 134b.

The presence of dishing and erosion are problematic for a number of reasons. The sum of dishing and erosion constitutes metal loss of lines 138. Metal loss raises the resistance of such lines, where resistance is typically critical because the lines are narrow. The higher resistance can degrade device performance. Dishing and erosion also cause an undesirable lack of planarity. Lack of planarity on the current polished surface frequently leads to lack of planarity of the next, higher polished surface, especially when the processes that deposit the overlying layers are conformal and not planarizing. Thus, locations over dished or eroded regions are lower than the surrounding areas and prone to having residue, which is a severe problem, as discussed above. Finally, lack of planarity on the overlying surfaces can degrade the results of microlithography. As device sizes shrink, the wavelength of light used in photolithography has decreased, and the numerical apertures of the lenses has increased, leading to a reduced depth of focus. This means that the distance between the lens and the substrate being exposed is a critical process parameter. If the substrate is not planar, it is impossible to have the whole surface exposed while in proper focus. Again, lack of focus during lithography can either degrade device performance, or in severe cases, result in non-functional devices. Dishing and erosion, once detected on a particular substrate, can not be repaired. Thus, the CMP process must be designed and controlled to minimize dishing and erosion.

The most effective method presently available for measuring dishing and erosion is with a stylus profiler or other scanning profiler, like an atomic force microscope (AFM). Unfortunately, these measurements have a number of disadvantages for routine use during the fabrication. They tend to be slow, and therefore delay the manufacturing process. As they employ contact or near contact, their use on product samples is generally regarded as a risk. The measurements are very sensitive to vibration, and thus not well suited for integration into a CMP cluster tool, if that is desired. Accordingly, it would be preferred to have a non-contact, fast, vibration- insensitive way to measure erosion and/or dishing.

Finarov et al. disclose in U.S. Pat. No. 6,100,985 (the '985 patent) an optical method and apparatus suitable for measuring erosion and residue on arrays (hereinafter referred to as "the Finarov technique"). The '985 patent is incorporated by reference herein. As illustrated in FIGS. 6a and 6b, the Finarov technique involves illuminating periodically patterned sample (array) 301 with broadband light beam 308 over a spot 310 that is larger than the pitch of the array defined by the spatial alternation of at least two zones 304 and 306. The technique detects the intensity of specularly scattered light from the array, and fits a simple model to the detected spectrum in order to measure at least one parameter (e.g., film thickness) of the array.

A suitable apparatus 320 for practicing the Finarov technique is shown in FIG. 7. Illuminator 322 emits light 324, which is deflected by beamsplitter 326 towards sample 321. Focusing element 328 focuses light 330 onto sample 321, and collimates reflected light 332, which passes back through beamsplitter 326. Turn mirror 334 deflects the collimated light 336 through second focusing element 338. Aperture stop 340 is substantially in an aperture plane for optical system 320, so that it limits light that is detected by a spectroscopic detector system 344 to only specular reflections from sample 321. Processor 346 processes the spectroscopic, specular data from detector system 344 to measure at least one parameter of sample 321.

The requirements for detecting specularly scattered light can be understood with reference to FIG. 8. Plane 348 represents an aperture plane of the optics, where distance from axis 352 represents the angle of light at sample surface 350 measured from axis 352, with positive angles corresponding to clockwise rotation about the intersection of surface 350 and axis 352. The illumination cone 351 in the aperture plane extends from point $a_1$ identified by location 354 to point $a_2$ identified by location 356. The reflected light is broken into diffraction orders by periodic array 350. The specular or zeroth order reflected cone overlaps incident cone 351, with the illumination ray eminating from $a_1$ giving rise to a reflected ray reaching the aperture plane at $a_2$, and vice versa, for the illustrated situation of quasi-normal illumination, i.e., where the axis of the illumination cone lies substantitally along axis 352. 'Specular' means "as from a mirror". This is the only component of light that would be reflected from a mirror. Non-specular reflected cone 363 represents first-order diffracted rays which exend on the aperture plane from point $b_1$ identified by location 364 to point $b_2$ identified by location 366. The Finarov method is particularly directed towards periodic samples. For such samples, non-specular light is reflected as discrete orders, as is well known in the art. The distance of a point on aperture plane 348 from axis 352 is proportional to the sine of the angle of a ray that passes through that point. For simplicity of notation, the constant of proportionality is taken as unity without loss of generality. It would have some other value in a practical situation. The sine of a diffracted ray of order n due to an incident ray of sine a is given as $$b = a + nd \qquad \text{Eq. 1}$$

where d=w/p is the ratio of wavelength w and period p of array 350. Thus, the illumination ray emanating from location 354 gives rise to the scattered first-order (n=1) ray reaching aperture plane 348 at location 364, and the illuminating ray from 356 gives rise to the scattered ray at 366.

The Finarov technique places stop 340 in the detection optics so that only rays that reach aperture plane 348 between points $c_1$ identified by location 360 and $c_2$ indentified by location 362 reach detector 344. The necessary constraint for the placement of $c_2$ so that only specular rays are detededed applies for the shortest wavelength $w_1$ and first-order ray at $b_1$ 364 which is closest to axis 352:

$$c_2 < b_1 \qquad \text{Eq. 2}$$

In order to generalize this constraint, it is convenient to define the numerical apertures $a_0$ of the illumination optics and $c_0$ of the detection optics so that $a_1 = -a_0$, $a_2 = a_0$, $c_1 = -c_0$, and $c_2 = c_0$. Then, the general constraint to insure substanitally specular detection of light reflectected by sample 301 is:

$$a_0 + c_0 < w/p \qquad \text{Eq. 3}$$

The constraint in Equation 3 has several disadvantages. First, the method requires that the sample have a periodic structure. It does not apply to aperiodic sample structures where diffraction orders are not well defined. Also, it requires a priori knowledge of the sample pitch p. It also requires an adjustable stop, with the associated additional complexity of hardware, electronics and software to control the stop. Finally, the constraint reduces the amount of light that reaches the detector and contributes to the measurement. In other words, it reduces the signal-to-noise ratio of the system, all else being equal. Collecting light at the detector for a longer time can improve the signal-to-noise ratio, but would reduce the throughput of the system, which is undesirable in a manufacturing environment.

SUMMARY OF THE INVENTION

The present invention pertains to processing wafers, and in particular to measuring parameters indicative of the quality of the wafer processing.

An object of the present invention is provide the optical method and aparatus to measure at least one parameter of a structure which is heterogeneous over the spot size of the optical system with as few limitations on applicability and design of the optical system as possible, and requires as little a priori information about the sample as possible.

It is another object of the present invention to provide a fast and robust means for characterizing dishing, erosion and residue of structures employed in microelectronic devices, e.g., integrated circuits. Depending on the situation in the factory, the hardware to make such measurements could be integrated into a process tool, such as a tool for chemical mechanical polishing (CMP), or on its own platform as a stand-alone tool.

It is another object of the present invention to provide a way to control the fabrication of microelectronic devices to minimize the occurance of dishing and erosion, on the one hand, and residue, on the other. Control of the process involves measuring the results of a process step and either feeding those results back to adjust the process for subsequent samples, or feeding the information forward to adjust subsequent processing steps.

Accordingly, a first aspect of the present invention is a method of measuring at least one parameter associated with a portion of a sample having formed thereon one or more structures with at least two zones each having an associated zone reflectance property. The method includes the steps of illuminating the zones with broadband light, and measuring at least one reflectance property of light reflected from the at least two zones. This reflectance property may be, for example, intensity. The measurement includes a substantial portion of non-specularly scattered light, thereby increasing the quality of the measurement. The method further includes the step of fitting a parameterized model to the measured reflectance property. The parameterized model mixes the zone reflectance properties of the zones to account for partially coherent light interactions between the two zones.

A second aspect of the invention is a method of measuring at least one final measured parameter associated with a portion of a sample having formed thereon having one or more structures. The method includes the steps of illuminating the sample at a first location with broadband light, and measuring at least one reflectance property of light reflected from the first location. The method further includes the steps of illuminating the sample at a second location having at least two zones, with broadband light and measuring at least one reflectance property of light reflected from the at least two zones. The next steps include fitting a first parameterized model to the first reflectance property to obtain an intermediate measured parameter, and fitting a second parameterized model to the second measured reflectance property based upon the first measured parameter.

The second reflectance model accounts for light interactions the at least two zones to obtain a value for the at least one final parameter.

BRIEF DESCRIPTION OF THE DRAWINGS

FIG. 11b is a plan view of the three-dimensional array of polysilicon plugs of FIG. 11a;

FIG. 19b is a cross-sectional side view of the collection of measurement spots of FIG. 19a;

FIG. 20b is a cross-sectional side view of the collection of measurement spots of FIG. 20a;

DETAILED DESCRIPTION OF THE INVENTION

The present invention pertains to processing wafers, and in particular to measuring parameters indicative of the quality of the wafer processing.

Figure 6A:
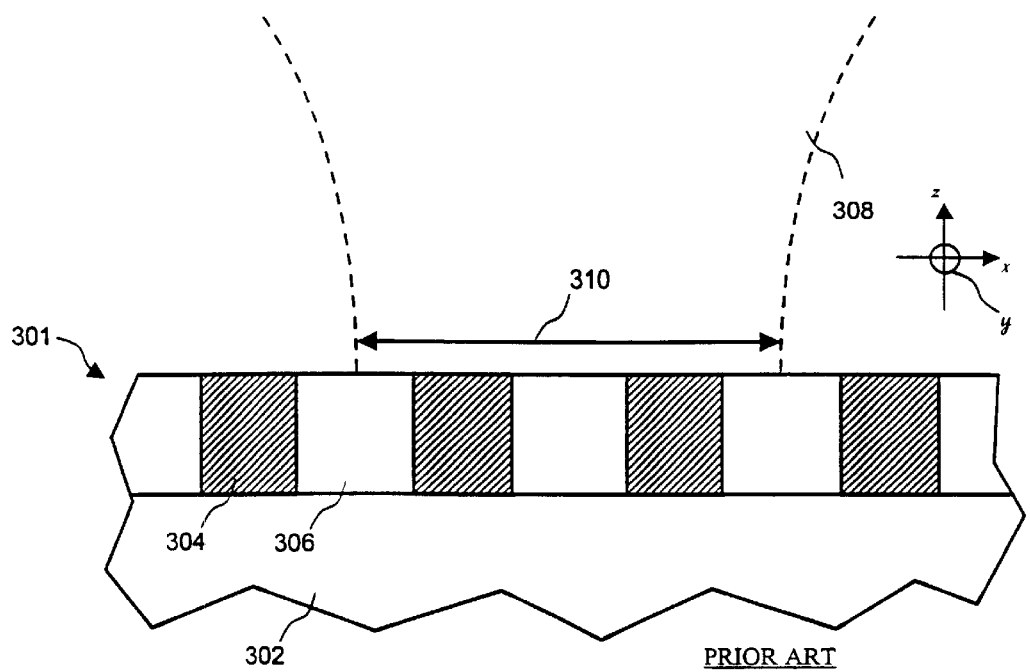
FIG. 6a is a schematic side view of an array being inspected by a beam of light.
Figure 6B:
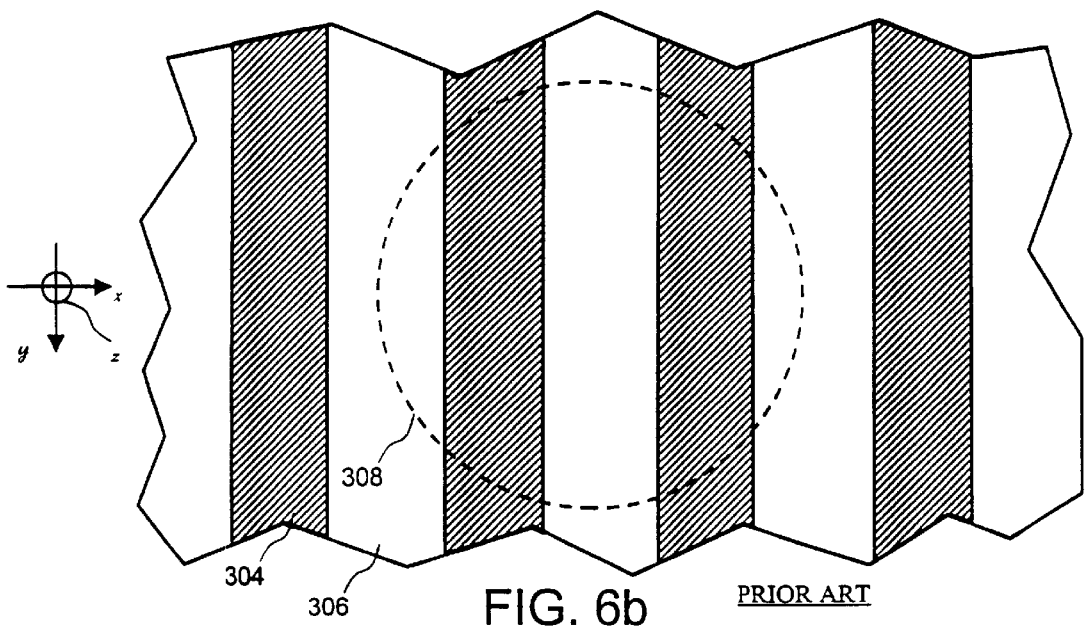
FIG. 6b is a schematic plan view of an array being inspected by a beam of light showing the spot on the array that is seen by the instrument.
Figure 9:
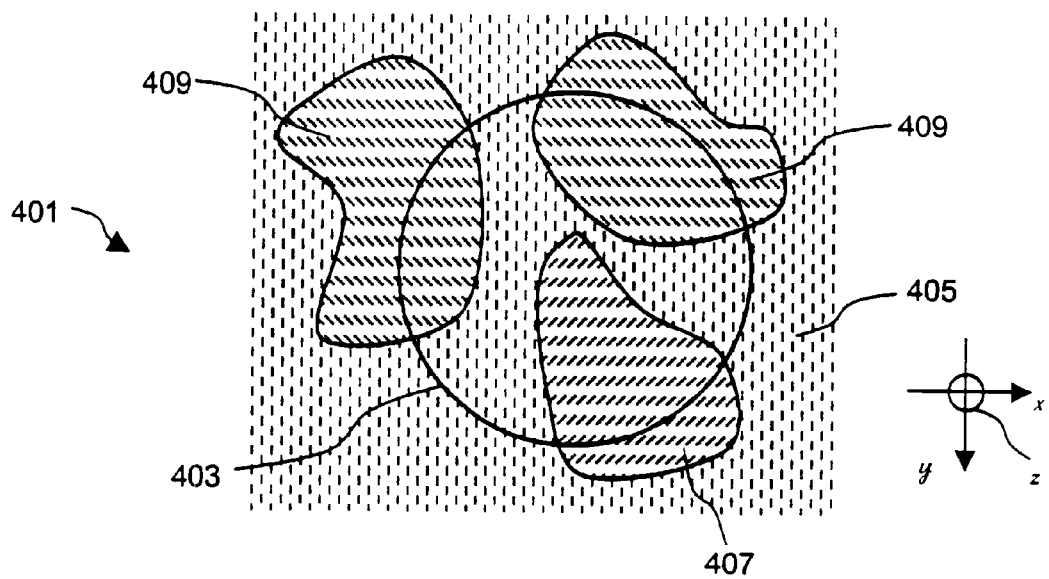
FIG. 9 is a plan view showing a measurement spot over multiple zones of a sample.
Figure 10:
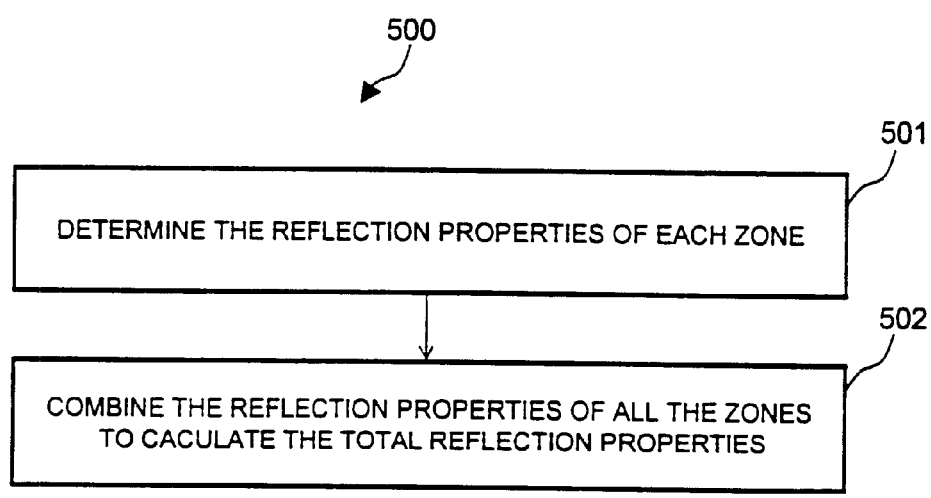
FIG. 10 is a flow diagram of the first embodiment of the present invention, describing the mixing of measurements taken from different zones to calculate an effective reflectance.

A first and simplest embodiment of the present invention may be understood with reference to FIGS. 9 and 10. FIG. 9 is a plan view of a sample 401, and FIG. 10 is a flow diagram for calculating the total reflection properties of the sample. Optical spot 403 defines the region interrogated by an optical measurement system, such as that shown in FIG. 6a. The sample includes of a collection of at least two zones, e.g., zones 405, 407, and 409 in this example. With reference to FIG. 10, in step 501 the individual reflection properties of each zone are determined independently. In step 502, the collective reflection properties of the spot are calculated from the individual reflection properties.

The zones may be connected, as is the case for zones 405 and 407, or disconnected, as is the case for zone 409. Each zone is assumed to have uniform reflection properties over its surface. Rather large deviations from perfect uniformity may be acceptable in many cases. For example, for a manufactured part there may transition regions between the zones, and these might be ignored without affecting the measurement. The zones may or may not form a periodic structure. This is an advantage over the Finarov technique, where the zones are constrained to be periodic. The Finarov technique necessarily rejects the use of non-specular components in the optical system with the use of an aperture, as described above. In order to calculate the size of the aperture, the sample must be periodic so that the size of the aperture can be calculated based on the locations of non-specular orders in the aperture plane. The reflections from an aperiodic sample are not easily separated into discrete orders. Mathematically, the scattered energy can be viewed as existing over a continuum of orders. Thus, an aperiodic sample generally scatters non-specular reflections to all locations of the aperture, so that it is unsuitable for the Finarov technique.

Figure 11A:
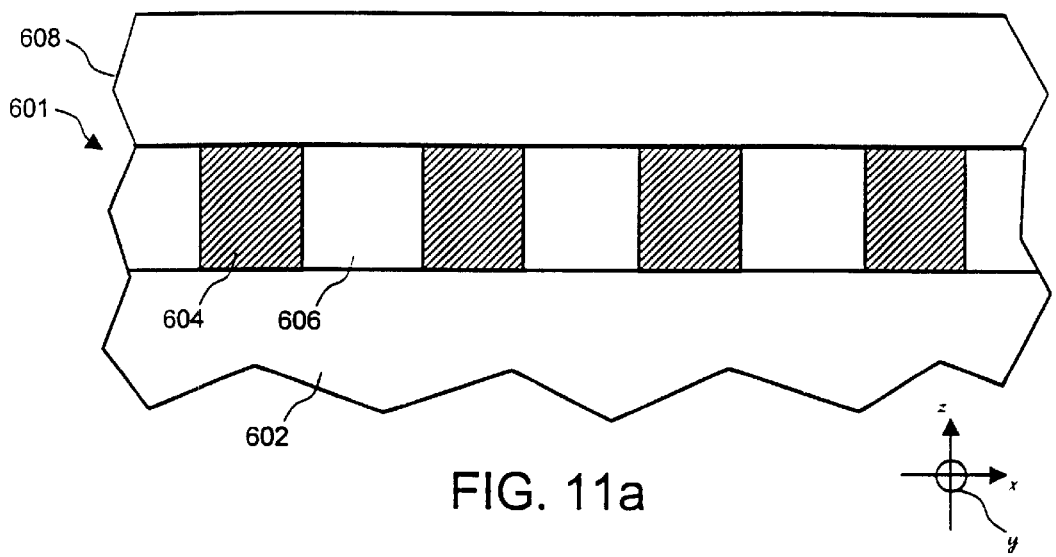
FIG. 11a is a schematic side view of a three-dimensional array of polysilicon plugs formed in a wafer.
Figure 11B:
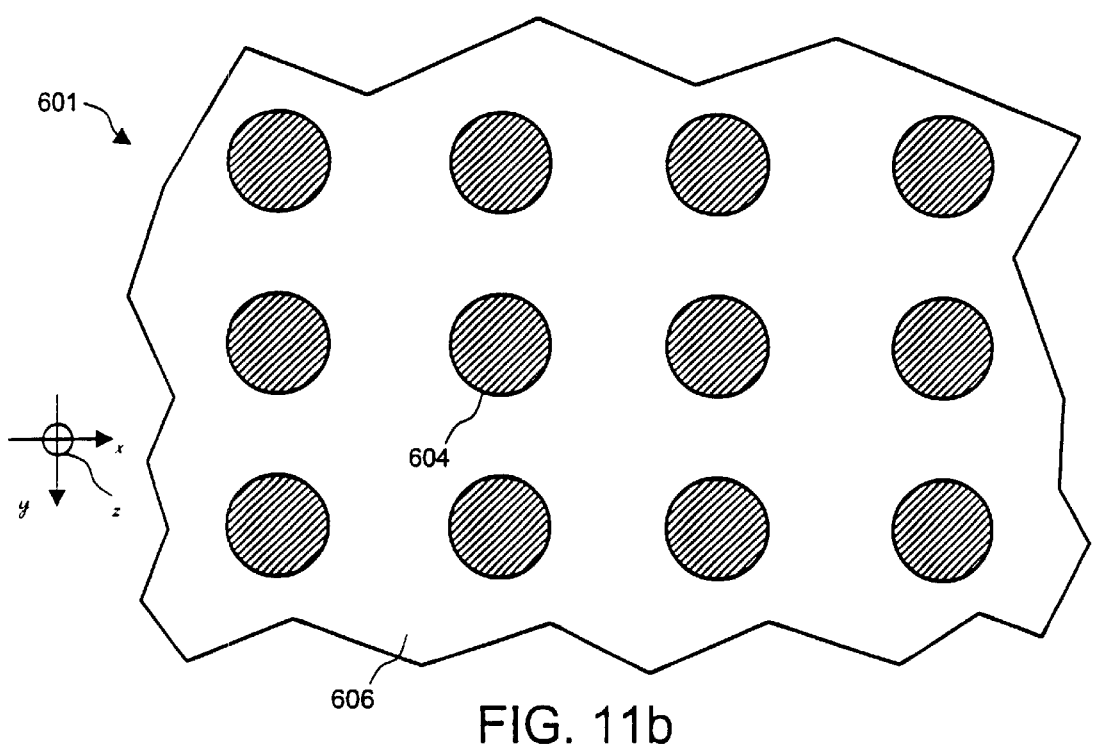

Each zone can take a variety of forms. In the simplest case, the top surface of the zone is an opaque reflector. For example, zone 304 in FIG. 6a may be made of copper with a thickness (in the z direction) of 1 micron. A more complicated zone would have one or more transparent layers over a substrate. For example, if region 306 of FIG. 6a were silicon dioxide (oxide), and region 302 were silicon, the oxide would be a transparent layer over the silicon substrate. In an even more complex situation, a zone may include a region that is heterogeneous in two or three dimensions. An example is shown schematically in FIGS. 11a and 11b, wherein polysilicon plugs 604 are separated by oxide 606 and buried under an oxide layer 608. This type of zone constitutes a three-dimensional grating.

The reflection property of a zone is preferably represented in mathematical terms by its complex reflection coefficient. While this may be defined in many different ways, a common and suitable definition would be the reflection coefficient for electric field, r, which is defined by the equation:

$$E_R(w) = r\, E_I(w) \qquad \text{Eq. 3}$$

where $E_I$ (w) is the complex amplitude of the electric field incident on the reflecting surface at wavelength w and $E_R$ (w) is the complex amplitude of the reflected electric field. In the simplest case, r represents the reflection coefficient of a single plane wave, although it may also be an effective reflection coefficient for a range of angles. An alternative reflection property is the intensity reflectance R, which is defined by the equation:

$$E_R(w) = R\, E_I(w) \qquad \text{Eq. 4}$$

where $I_I$ (w) is the incident intensity at wavelength w falling on the reflecting surface and $I_R$ (w) is the reflected intensity. The reflectance is the squared magnitude of the reflection coefficient:

$$R=|r|^2 \qquad \text{Eq. 5}$$

Thus, the reflectance is a real number and contains less information than the reflection coefficient, lacking information about phase implicit in the complex reflection coefficient.

The reflection property is ideally determined from a theoretical calculation. This is straightforward for the first two types of zones Z discussed above, i.e., the opaque surface and the layer stack. These calculations are well known in the art, and are discussed in the article by P. S. Hauge, entitled "Polycrystalline silicon film thickness measurement from analysis of visible reflectance spectra," J. Opt. Soc. Am., Vol 69, No. 8, August 1979. In this case, the optical properties of the layers (if any) and the substrate, as well as the thicknesses of the layers (if any) must be known or assumed. In the case of more complex structures there are also known methods. For periodic structures in one lateral dimension (e.g., x) the methods of Li (e.g., Lifeng Li, "A modal analysis of lamellar diffraction gratings in conical mountings,", Journal of Modern Optics, 1993, Vol. 40, No. 4, 553–573, are appropriate. With heterogeneity in two lateral dimensions, i.e., x and y, the methods of Cwik ,e.g., T. Cwik, J. Z. Lou and D. S. Katz, "scalable, Finite Element Analysis of Electromagnetic Scattering and Radiation," *Advances in Engineering Software,* vol. 29, pp 289–296, 1998, may be employed. In all these cases, the optical properties of all illuminated structures and a complete description of the geometry must be known.

Figure 12:
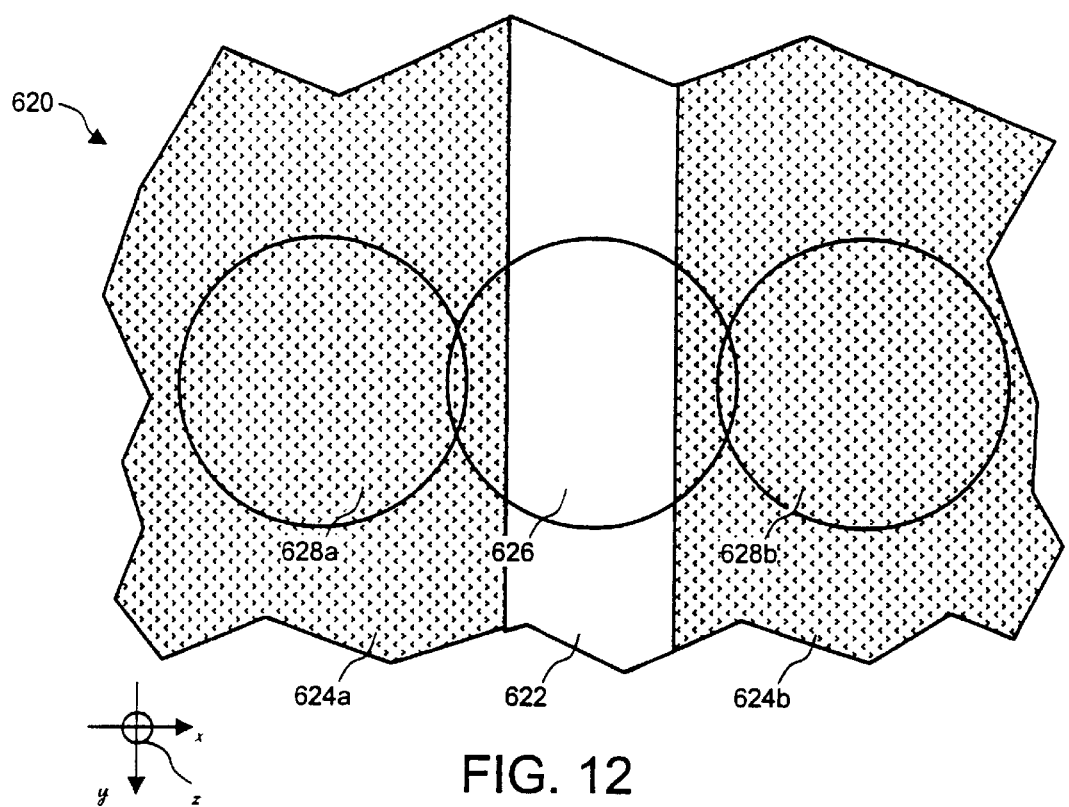
FIG. 12 is a plan view of a wafer having a uniform layer stack surrounded by three-dimensional gratings, showing three measurement spots suitable for measuring at least one parameter of the uniform film stack.

An alternative approach to determining the reflection properties is to measure them directly. With reference to FIG. 12, sample 620 has three zones, 622, 624a and 624b. In this case, zone 622 is a layer stack, and its reflection coefficient can be calculated. However, zones 624a and 624b are heterogeneous in both the x and y directions, and calculating their reflection properties would be difficult. Zones 624a and 624b are nominally the same, but may differ somewhat due to manufacturing tolerances. The exemplary goal is to model the signal from measurement spot 626, and measure the thickness of at least one of the layers in stack 622. In this case, the signal from spots 628a and 628b can be measured and used to calculate the reflection properties (e.g., the reflectances) of zones 624a and 624b.

As mentioned above, step 502 of flow diagram 500 of FIG. 10 calculates the total reflection properties from the reflection properties of the different zones. Preferably the total reflectance $R_T$ is calculated by "mixing" the reflection coefficients of the different zones: $r_1$, $r_2$, etc. The phase of each reflection coefficient varies with height relative to the film substrate, so the reflection coefficients are defined relative to a specific plane at a particular height. The mixing can be incoherent, coherent, or partially coherent. For the case of purely incoherent mixing, the total reflectance has the form $$R = A_1|r_1|^2 + A_2|r_2|^2 + \qquad \text{Eq 6}$$

wherein the coefficients $A_1$, $A_2$, etc. depend on the fraction of the beam area intercepting each corresponding reflection zone and the beam intensity distribution over each zone and K represents any similar terms for additional zones. This form of mixing can be used for the example associated with FIG. 12. For the case of purely coherent mixing the signal amplitudes, rather than intensities, are additively superimposed at the detector, so in this case the total reflectance has the form $$R = |a_1 r_1 + a_2 r_2 + \ldots|^2 \qquad \text{Eq 7}$$

wherein the coefficients $a_1$, $a_2$, etc. are complex-valued. This equation can be expanded to obtain the following equivalent expression, $$R = \left(\sum_j A_j |r_j|^2\right) + \left(\sum_{j,k(j<k)} B_{j,k}\mathrm{Re}[r_j r_k^*] + C_{j,k}\mathrm{Im}[r_j r_k^*]\right) \qquad \text{Eq 8}$$

wherein range of the indices is over the number of zones in the spot and $$A_j = |a_j|^2 \qquad \text{Eq 9}$$

$$B_{j,k} = 2\mathrm{Re}[a_j a_k^*] \qquad \text{Eq 10}$$

$$C_{j,k} = -2\mathrm{Im}[a_j a_k^*] \qquad \text{Eq. 11}$$

In the above equations, Re[z] represents the real part of a complex quantity z, Im[z] represents the imaginary part of z, and z* is the complex conjugate. The general case of partially coherent mixing is also described by Eq. 8, except that in this case the $A_j$, $B_{j,k}$ and $C_{j,k}$ coefficients do not obey Eqs 9–11. However, they would be constrained by the following conditions:

$$|B_{j,k}| \leq 2|A_j A_k| \qquad \text{Eq 14}$$

$$|C_{j,k}| \leq 2|A_j A_k| \qquad \text{Eq 13}$$

The "mixing coefficients" $A_j$, $B_{j,k}$, and $C_{j,k}$ must also be known in order to execute step 502. They can be determined geometrically to accommodate variability of the beam energy distribution on the film and the beam's alignment relative to the pattern. In general, the coefficients may be functions of wavelength.

Figure 13:
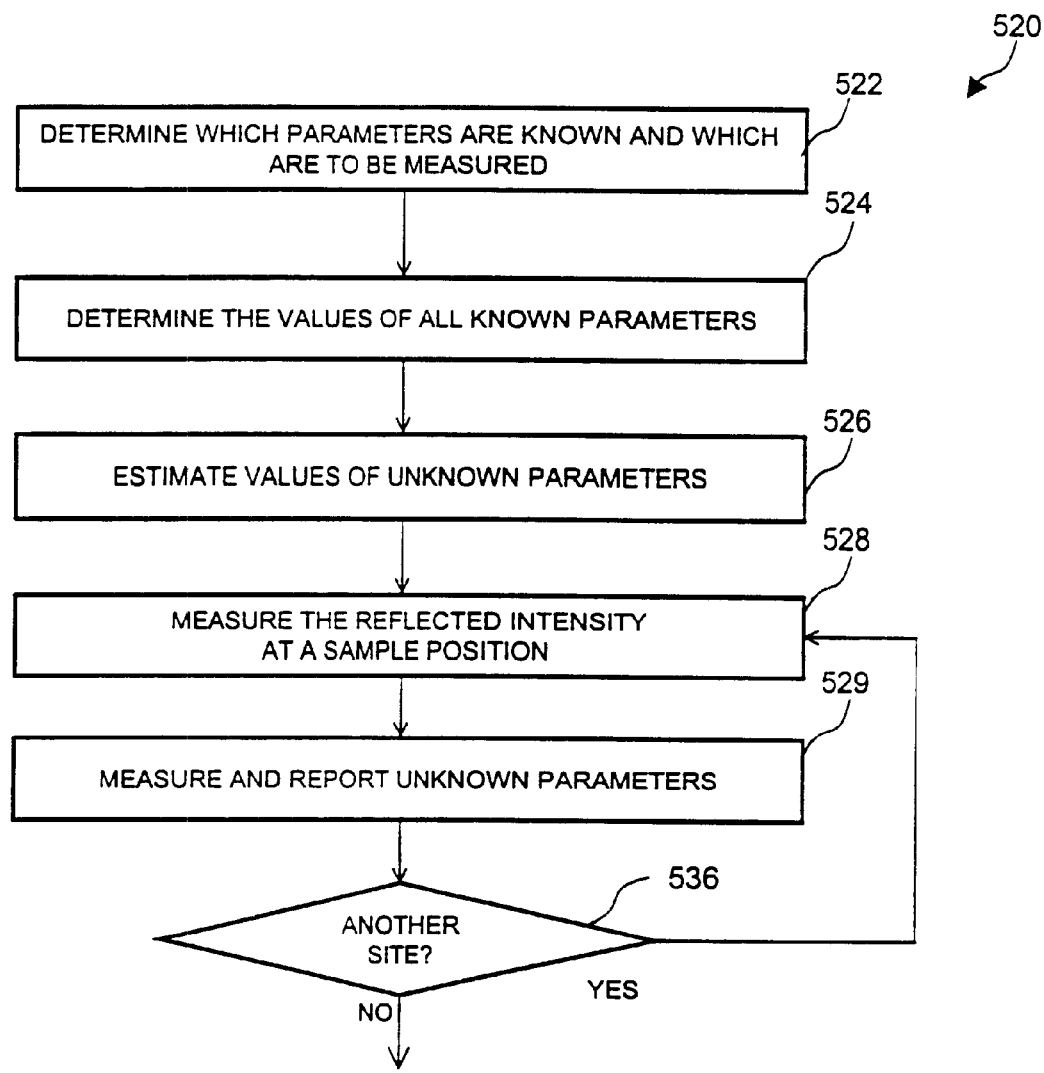
FIG. 13 is a flow diagram for a second embodiment of the present invention incorporating the mixing model of FIG. 10.

With reference to FIG. 13 and flow diagram 520, in a second embodiment of the invention, the flow diagram 500 of FIG. 10 is embedded in flow diagram 520 routine 520 to measure at least one of the parameters in the model of step 500.

In step 522 of flow diagram 520, all the parameters needed to calculate the total reflectance are identified as either known or unknown. Parameters include the optical indices of all media that are illuminated, all significant geometric parameters, and the mixing parameters discussed above. The optical indices may be expressed as either functions of one or more parameters, as a table of values, or by some combination of the two methods. The precise form of the mixing parameters is chosen. Also the wavelengths to be considered are chosen.

In step 524, the values for all the known parameters are determined. These may be determined by measurements, experience, theoretical considerations, or any other means.

In step 526, estimated values are assigned to all the unknown parameters. These may be determined by measurements, experience, theoretical considerations, or any other means. In some cases, a set of values may be assigned to a particular parameter.

In step 528, the light reflected from the sample over the spot of the measurement instrument is measured.

Figure 14:
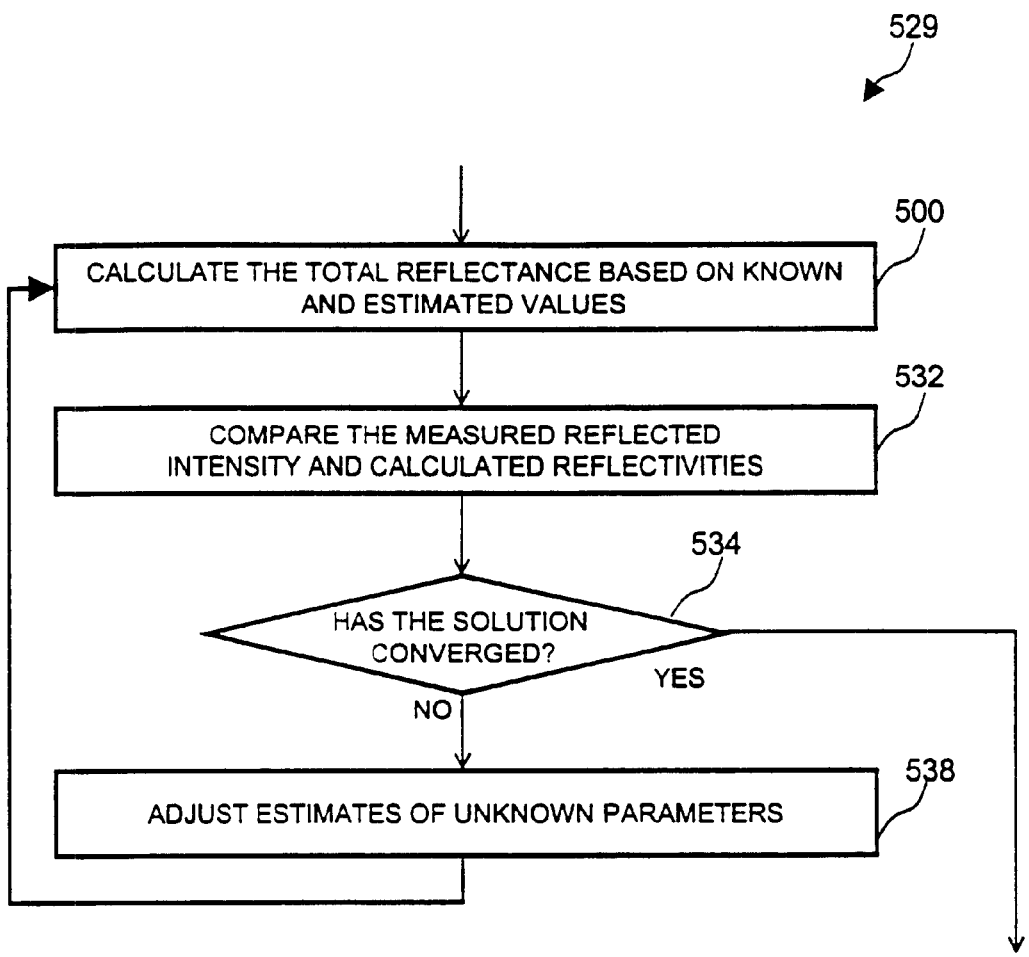
FIG. 14 is an expanded flow diagram of step 529 of FIG. 13 detailing the measurement of at least one parameter.

In step 529, the unknown parameters are measured, as described in more detail in FIG. 14. The first sub-step within step 529 is flow diagram 500. The total reflectance of the sample is calculated based on known and current estimates of unknown parameters. If some of the unknown parameters have multiple estimates, all possible combinations of estimates are used to calculate a set of possible total reflectances.

With continuing reference to FIG. 14, in step 532, the measured reflected light and the calculated total reflectance are compared. This is preferably done using a weighted least-squares error approach, as described in greater detail in U.S. patent application Ser. No. 09/533,613, filed on Mar. 22, 2000, which is incorporated by reference herein. This weighted least-squares error is given by:

$$E^2 = \Sigma[(P_1 - P_2 R_M)/Z]^2 \qquad \text{Eq. 14}$$

where the sum is over wavelengths, $P_1$ is a spectral product of measured (and possibly subtracted spectra) proportional to the reflectivity of the sample and $P_2$ is a spectral product which is proportional to instrument effects which may also be proportional to spectral product $P_1$, and Z is a wavelength dependent weighting function. In a simple case $P_1$ may be the "measured" reflectivity and $P_2$ taken as all ones. Z may be taken as all ones, but is preferably proportional to the uncertainty of measurement at each wavelength, or some approximation to this.

In step 534, the current (and, in some cases, previous) results are examined to determine if the solution for the reflectivity has converged. Convergence is preferably determined dynamically by examining the change in the error and/or the change in the values assigned to the unknown parameters to determine if there has been any significant improvement or change, respectively. If there has been no improvement, or if the changes are insignificant, then the solution is deemed to have converged.

Convergence may also be determined by checking to see if $E^2$ or some function thereof satisfies a predetermined condition. This method of comparing parameters to a predetermined value has several disadvantages, which include the fact that several solutions may exist that satisfy the predetermined condition. Further, there may be no solutions that satisfy the predetermined condition, or that significant effort must be devoted to determining an appropriate predetermined condition.

If the solution has converged in step 534, then step 536 (FIG. 13) determines if there is another sample location to be measured with this algorithm. If there is no other sample to be measured, the process is terminated. If there is another sample location to be measured, process 520 returns to step 528.

If the solution for the reflectivity has not converged in step 534, then step 538 adjusts the unknown parameters for another iteration of the loop by returning the process to step 530. There are many methods known in the art for adjusting the parameters in step 538 in order to quickly obtain convergence in step 534, such as the method of Marquardt and Levenburg.

In step 538, Equations 9, 10, and 11 may be optionally imposed as optimization constraints.

For process 520, there are two classes of unknown parameters. one or more unknown parameters will be relevent to evaluating the manufacturing process in question (e.g., CMP), and so are desired to be known. The goal is to measure these parameters. There is another class of unknown parameters that are not of particular interest in that they are not relevent to the process in question. There may be none, or one or more of these parameters, depending on the situation. An example would be polysilicon plugs 604 in FIG. 11a, where only the thickness of top layer 608 would be of interest for characterizing a CMP process. However, "irrelevant" unknowns must be measured along with the relevent unknowns in order to allow the mixing model to accurately conform to the physical situation. The one or more parameters (of both classes) may include those relating to the optical properties of the media making up the layers, the thicknesses of layers, and the mixing coefficients.

Figure 15A:
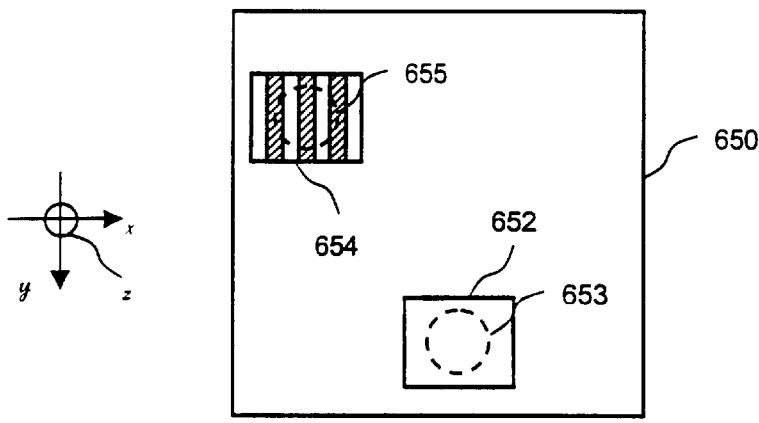
FIG. 15a is a plan view of a collection of two measurement spots used to characterize two different regions of a sample, the two regions constituting a simple film stack and a grating, respectively.
Figure 15B:
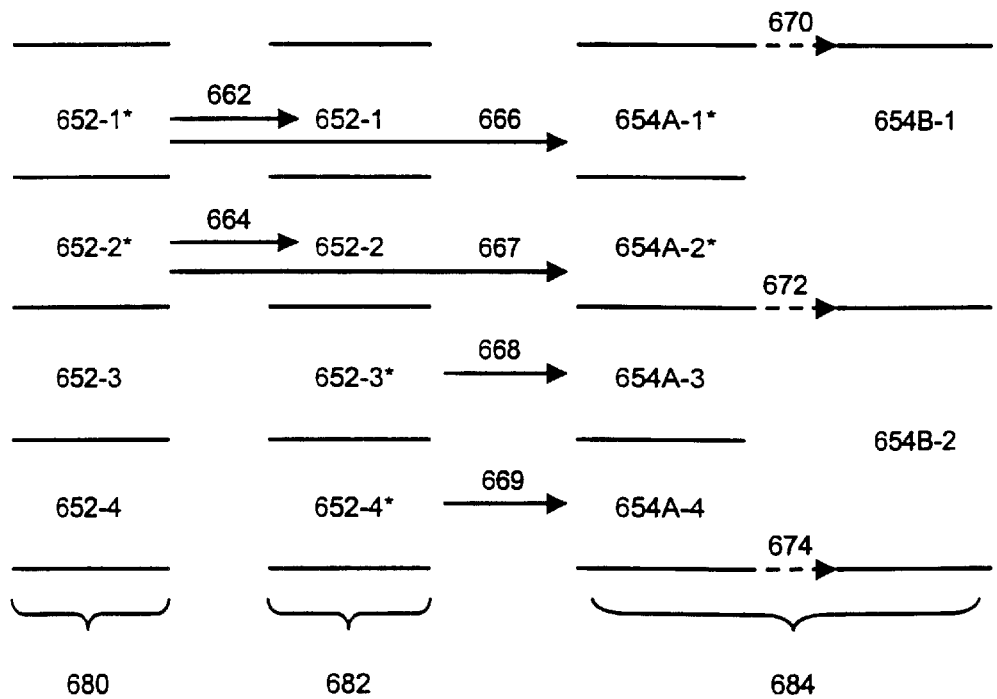
FIG. 15b is a diagram of a chain algorithm for processing a data from a collection of measurement sites.
Figure 16:
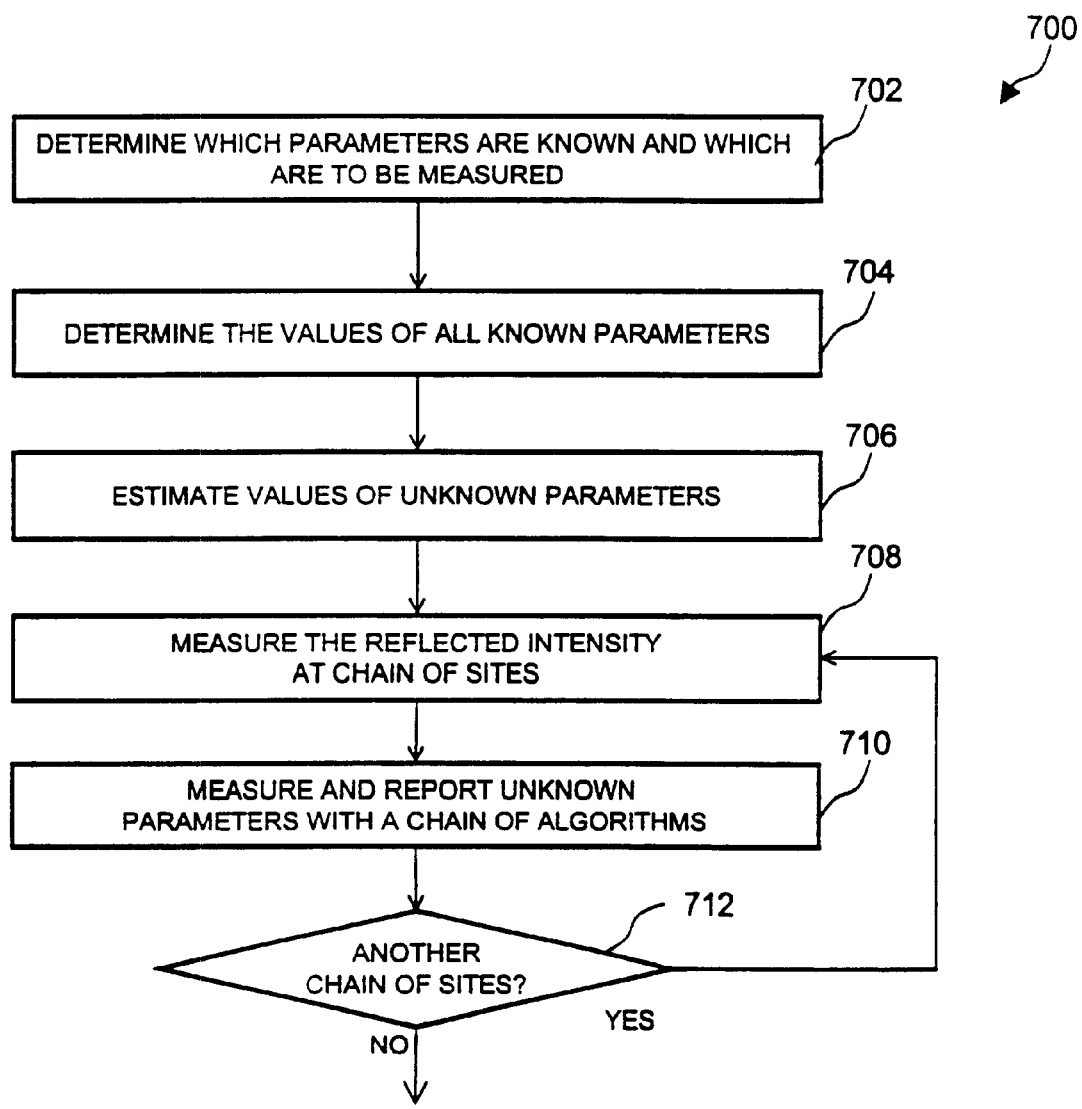
FIG. 16 is a flow diagram of the steps associated with a third embodiment of the present invention involving a chain algorithm applied to a collection of measurement sites.

With reference to FIGS. 15a, 15b and 16, an example of a third embodiment of the present invention that uses a collection of sites and a chain of algorithms to measure unknown wafer parameters of interest is now described. FIG. 16 shows the flow diagram for a more general procedure. With reference to FIGS. 15a and 15b, die 650 on the wafer contains two sites of interest, 652 and 654. These sites are regarded as a collection of sites, i.e, they are measured sequentially over spots 653 and 655, respectively, and then processed together by a chain of algorithms. As the term is used herein, a chain or collection of algorithms comprises a set of algorithms that are linked by passing parameters of one algorithm to another algorithm in the chain or collection. The parameter may become either a fixed value in the destination algorithm, or an initial estimate for that algorithm. Site 652 comprises a stack of uniform films, and site 654 is an array, as described above. In general, site 652 is easier to measure and would be expected to give more reliable results.

Thus, if any of the parameters that would be unknown at site 654 can be measured at site 652, the results are likely to be more reliable. Also, the speed of the total measurement can be improved by making several measurements with fewer unknown parameters than one measurement with all the necessary unknown parameters.

The value of the abovementioned approach can be appreciated if one considers using a simple library to solve the measurement problem. In the library approach, a set of reflectivities is calculated to cover all possible unknown parameter combinations. The error for each calculated reflectivity given the measured spectral products is calculated.

The parameter values for the reflectivity with the least error are chosen as the measured values for the unknown parameters. Each parameter has an allowed range and a desired resolution, and thus, a number of samples associated with it. For example, if there are four parameters, there will be four numbers of samples, e.g.: $N_1$=100, $N_2$=100, $N_3$=100, and $N_4$=100. If one library is used to measure all the parameters, then it will have $N_1$ $N_2$ $N_3$ $N_4$=100,000,000 entries. If two libraries can be used in a chain, where each measures two parameters, there will be $N_1$ $N_2$+$N_3$ $N_4$=2,000 entries. This represents a savings in library size of a factor of 50,000. A similar savings in computation time would result for the iterative method described above.

FIG. 15b represents a chain of three algorithms, 680, 682 and 684, applied to the collection of measurement sites shown in FIG. 15a. Algorithm 680 is applied to site 652, as is algorithm 682. Algorithm 684 is applied to site 654. The lines (without arrows) in the Figure represent boundaries between layers, and thus the areas between lines represent layers. Site 652 has four layers: 652-1, 652-2, 652-3 and 652-4. For this example all layer thicknesses are parameters, and the same number will be used to designate a layer and its thickness. An asterisk indicates an unknown thickness, i.e., one that will be measured in a particular algorithm. Algorithm 680 measures layer thicknesses 652-1 and 652-2 as unknown parameters. In this example, layer 652-3 is lossy at short wavelengths, so that its thickness and the thickness of layer 652-4 below it have little affect on the reflectivity for short wavelengths. Therefore, algorithm 680 only considers short wavelengths, e.g., between 320 and 500 nm, when evaluating the error in Equation 14.

Algorithm 682 measures the thicknesses of the bottom two layers of site 652, as indicated by the asterisks. Solid arrows 662 and 664 represent parameter links to pass results from algorithm 680 to algorithm 682. Layers 652-1 and 652-2 are not regarded as unknown parameters in algorithm 682 so that the results from algorithm 680 are passed as fixed values to algorithm 682. Algorithm 682 operates at long wavelengths (again, with respect to evaluation of the error defined in Equation 14.), e.g., for 500 nm to 790 nm, where at least some of the light penetrates to the bottom of layer 652-4 and returns to the top of site 652 to be detected. The two wavelength ranges in this example do not overlap, but share a common wavelength. These conditions are not necessary; the wavelength ranges may overlap to any extent, or may be completely disjoint.

With continuing reference to FIG. 15b, algorithm 684 measures parameters of array site 654 using values from both algorithms 680 and 682. Site 654 has two zones, designated A and B, each with its own set of layers. Zone 654A has the same four layers as site 652. Zone 654B has different layers. Zone A may be an insulating dielectric zone that is essentially transparent, and Zone A may be a conductive metallic zone where at least layer 654B-1 is metallic and essentially opaque. Dashed arrows 670, 672, and 674 are height links that define the physical height relationships between the two stacks. Thus, thickness 654B-1 is forced to be the sum of thicknesses 654A-1 and 654A-2, at all times, and is not a separate parameter. Similarly thickness 654B-2 is fixed by height links 672 and 674. If layer 654B-1 is effectively opaque at all wavelengths, layer 654B-2 could be eliminated. This would not affect the results, as its thickness is not really an independent parameter. Thicknesses 652-1 and 652-2 measured by algorithm 680 are passed as estimates (or 'seeds') by parameter links 666 and 667 to algorithm 684.

The reason for this is based on process considerations. These two layers are expected to vary significantly either across a wafer or from lot to lot, but by only a small amount across a die. Thicknesses 652-3 and 652-4 from algorithm 682 are passed via parameter links 668 and 669 to algorithm 684 as fixed values. The process expectation is that these values may vary across a wafer or from lot to lot but not within a die. The mixing parameters, although not discussed in this example, are other parameters for algorithm 684. These may be known or unknown, depending on the particular situation.

Finally, although not indicated in FIG. 15b, the difference between the thickness of layer 652-1 measured by algorithm 680 and the thickness of layer 654A-1 measured by algorithm 684 may be regarded as erosion due to the presence of metal layer 654B-1. The example above can be modified in many ways. The ambient medium (typically, air, but, for the case of integrated measurements for a CMP tool, may be water) is the medium above all the layers in FIG. 15b. A layer of ambient medium can be added to a zone with an appropriate height link to model a surface height variation within a site from zone to zone. The substrate is the medium below all the layers in FIG. 15b. A layer of substrate can be added to a zone, with an appropriate height link, to model a base height variation within a site from zone to zone.

FIG. 16 sets forth a flow diagram of the steps for a general method for the third embodiment of the present invention, wherein a chain of algorithms operates on a collection of sites to obtain measurements of unknown wafer parameters. Steps 702, 704, 706, and 708 are like steps 522, 524, 526 and 528, respectively, of flow diagram 520, with the following differences. Step 702 includes determining which data goes with which algorithm. In steps 702, 704 and 706 there are known and unknown parameters for all the sub-algorithms in the chain, instead of for a single algorithm. In step 708, there are all the spots in the collection of spots instead of a single spot.

Figure 17:
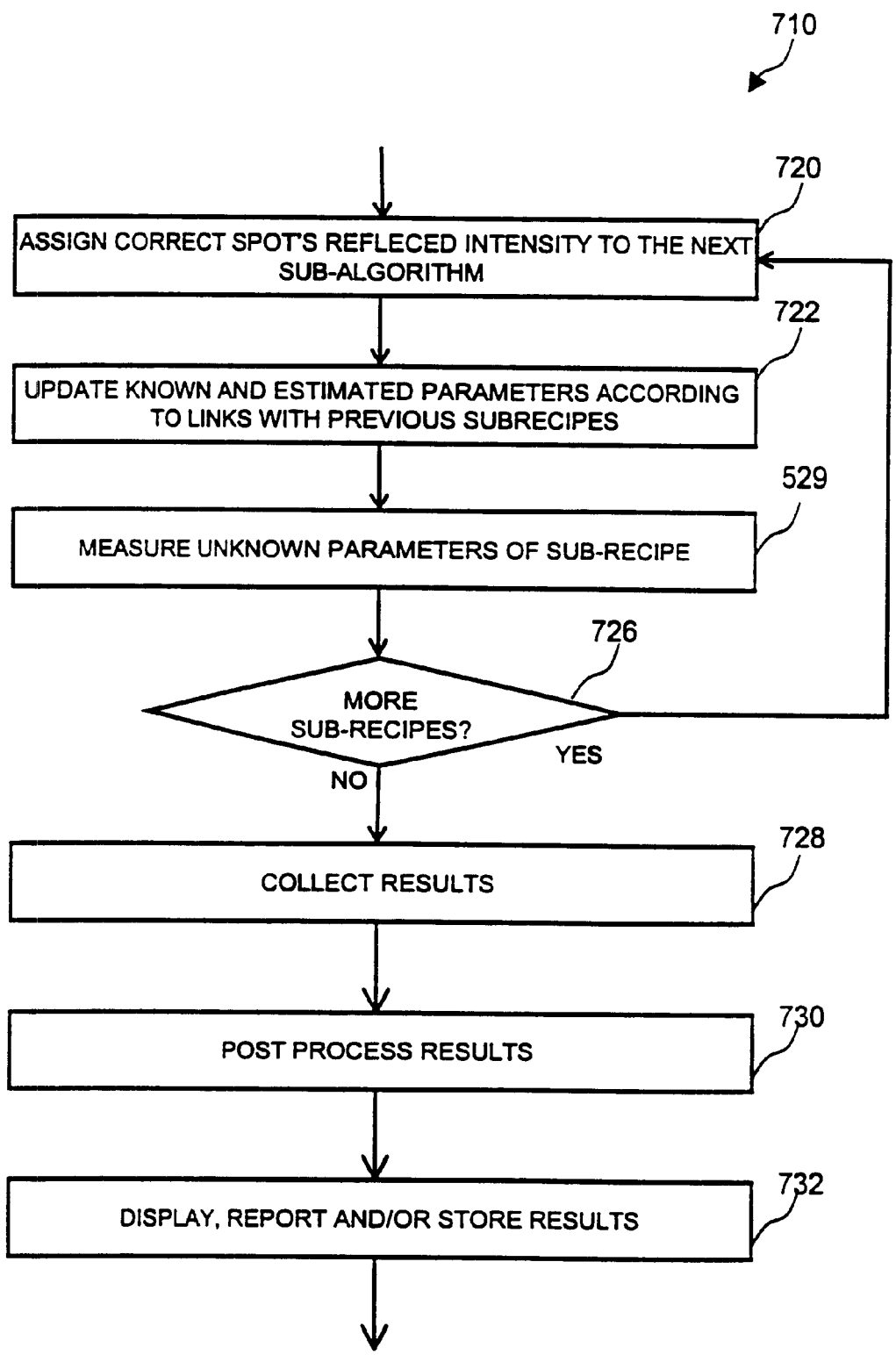
FIG. 17 is an expanded flow diagram of step 710 of FIG. 15 used to measure at least one parameter with a chain algorithm applied to a collection of sites.

Step 710 encompasses the processing of the results with the chain of algorithms, and is described in more detail below in connection with FIG. 17. Step 720 assigns measurement data at a particular spot to a particular algorithm, according to a predetermined rule from step 702. Step 722 takes results from previous sub-algorithms in the chain and applies them to the current algorithm before running that algorithm. This was discussed above, and shown graphically for the specific example in FIG. 15b by solid arrows. Step 529 is described above in conjunction with FIG. 14, and essentially involves the use of a particular algorithm on a particular data set with the linked previous results. The results are stored for later use. Step 726 goes to the next subrecipe if there are more sub-algorithms to be processed, or proceeds to step 728 if all the sub-algorithms have completed for a particular collection of measurements.

This third embodiment encompasses the second embodiment discussed above. In the case where there is only one sub-algorithm, the two embodiments are identical. Step 728 collects the results from all the sub-recipes and passes them on to on to the succeeding steps, e.g., optional step 730 to the succeeding steps, e.g., optional step 730. Optional Step 730 calculates additional results from the 'raw' results collected in 728. Step 732 delivers the results to a particular destination. In some cases, this destination may involve displaying the results in "real time", e.g., for an operator or applications engineer to see, either to evaluate the quality of the measurements or of a process that preceeded the measurements. Delivery may also include storing the results, e.g., in an archive or database that is later used for statistical process control. Finally, delivery may involve transfer of key results to a processor or other device responsible for control of a process tool.

In an alternate embodiment, data at each spot may be collected after previous spots have been partially or fully processed. In general, there is no required order of events other than the need to process a spectrum after it has been acquired.

Step 728 relates to the need to measure erosion described in the background. Measurements at at least two positions are needed to measure the erosion, one in a field area and one in an array. For example, with reference again to FIG. 15a, the measurement at spot 653 is suitable for the measurement in a field location, and the measurement at spot 655 is suitable for the array measurement. The difference between the two measured thicknesses, 652-1–654A-1, is the erosion. In this example, the material for layer 652-1 might be oxide, for 654B-1 copper, and the process designed to polish copper faster than the oxide, giving rise to erosion of the oxide in the array area.

The basic idea of measuring erosion by measuring thicknesses of transparent layers in a field and array location is not limited to the use of the mixing algorithm or of normal incidence reflectometry, as described above.

Further, the "array" need not be a periodic structure. The underlying layers are not necessarily flat uniform layers. In some cases it may be advantageous to model underlying layers with the mixing algorithm. Also, additional a priori information about the geometry of the sample may be used in calculating erosion from measured thicknesses. Such a priori information may include, for example, a pre-measurement of the profile of the surface directly beneath the field and array using a stylus profilometer, or the present invention.

The array need not contain copper elements, and can include other metals, such as tungsten and aluminum. Also, all the zones in an array may be dielectric, as is the case for shallow trench isolation structures in microelectronics manufacture. In this case, the top materials in the two stacks are oxide and (silicon) nitride, and the polishing process is designed to polish oxide. Erosion of the nitride in arrays due to the presence of oxide is called "STI erosion," and dishing of the oxide is called "STI dishing." Other common multi-zoned structures include patterned gate contacts.

Figure 18A:
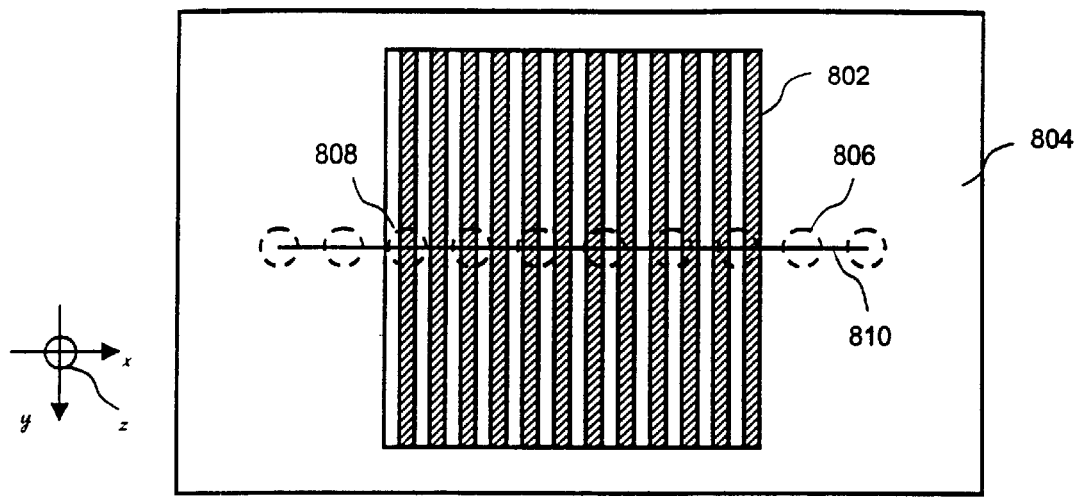
FIG. 18a is a plan view of a collection of measurement spots designed to characterize an array surrounded by a field, along with the trace of a profilometer for performing a similar characterization.
Figure 18B:
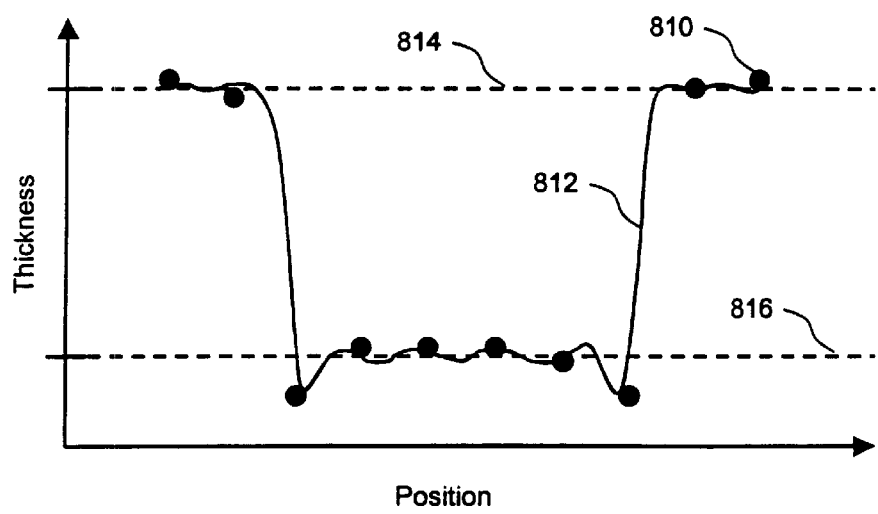
FIG. 18b shows measurements of array 802 from FIG. 18a with the present invention at sites 806 etc, and with a profilometer along trace 810.

The erosion measurement may use more than two beam positions, as shown in FIGS. 18a and 18b. In this example, array 802 is surrounded by field area 804. A collection of spots includes some spots like spot 806 that are in field 804, and some spots like spot 808 that are in array 802. For comparison, a stylus profile (possibly with an AFM) may be performed along scan line 810.

FIG. 18b shows an optical profile 810 and an overlayed stylus profile 812 for comparison. The stylus profile has been "leveled" with a quadratic function fit to the field areas at either end of the profile, and shifted so that points in the field roughly match the optically measured thickness 814 in the field. The array part of the profile is nominally at level 816. The stylus profile may or may not show dishing in the array as a ripple, depending on the sampling interval of the profile and the geometries of the stylus and the array. The optical profile does not require leveling, in general. If there was a difference in thickness of the two field areas, the optical profile could be leveled, or preferably, the stylus profile would be matched to the optical levels at each end. For both profiles, a single number representing erosion is somewhat ambiguous, and various means of calculating 'erosion' are possible, including using the maximum height difference, the mean of field thicknesses minus mean of array thicknesses, and the mean of the outer field points minus the central array point.

In cases where a mean value is used, various approaches to picking the members to be averaged are possible. In some cases, it would be advantageous to exclude outliers, by means generally know in the art.

In another aspect of the present invention, test structures for measuring the amount of erosion are designed into the wafer. In the current art, test pads are typically placed in scribe lines between dies on a wafer to measure film thickness. In the present invention, an array structure, like array structure 802 shown in FIG. 18a, is placed in the scribe line to serves as the test structure. The parameters of the structure, are designed to allow robust measurement of erosion. The pitch, density, map geometry and underlying layers are chosen to allow a robust optical measurement, either with the mixing algorithm described above or some other optical technique. For the mixing algorithm, the lateral dimensions of transparent regions in the array are preferably greater than an optical wavelength. The underlying structure preferably has a flat reflective layer not too far below the layer of interest, to reduce the number of variables in the inversion process.

In another aspect of this invention, dishing is measured from a single beam position over the array. The reflecting stack in the copper zone of the array can be regarded as having a layer of the ambient medium (leg, air or water) over it, so that the stack height is uniform with that over the dielectric zone of the array. The thickness of this ambient layer is, or is closely related to, the amount of dishing. The "effective" thickness of the air layer, i.e., its apparent optical thickness, is affected by the details of the profile shape of the top surface of the array. These can be accounted for theoretically or empirically to obtain a dishing measurement from the apparent optical thickness of the ambient layer. The thickness of the ambient layer can be an inversion parameter, as it is implicitly contained in one of the reflection coefficients in Equation 8, i.e., the reflection coefficient describing the copper region.

In another aspect of this invention, erosion (or dishing) is measured at a many locations on a wafer, e.g., at each die where there is a similar site, to produce an erosion (or dishing) map. The map is a collection of measurements at known locations on the wafer. The map may be displayed in various ways, a contour plot, ashaded map, a three-dimensional surface plot, or a number map, with erosion (or dishing) values displayed in locations corresponding to the measurement locations.

In all cases interpolation between measured points may be used to make a display that is more pleasing or understandable to the eye.

For any of the models, including the mixing model, the modeled light may consist of more than one plane wave. A single incident plane wave and single reflected plane wave is the simplest approach. This can be refined by accounting for energy reflected in diffraction orders that fall within the numerical aperture of the optics. In addition, finite beams can be viewed as a collection of infinite plane waves. This is especially important for focused beams, where the angles of the plane waves cover at least the numerical aperture of the system. The effects of multiple plane waves are modeled in Equation 8 by incoherently integrating or summing over the reflection coefficients of the relevant plane waves, accounting for their propagation phase. Similarly, for incoherent illumination and detection, Equation 8 is summed incoherently for parallel and perpendicular polorizations.

The description above applies to the preferred embodiment where a reflectometer measures reflected intensity at near-normal incidence. Alternative embodiments employ other measured quantities from other optical instruments-Normal incidence reflectometry, as discussed above, is simple, fast and relatively inexpensive to implement. Other methods, such as ellipsometry, give different information about about the relfection properties of the sample at a cost of complexity, space requirements and/or measurement time. Ellipsometry typically measure the ratio of the reflection coefficients for parallel and perpendicular polarizations, or some function thereof, eg, the magnitude and phase of the ratio. See Rasheed M. A. Azzam, 'Ellipsometry' in *Handbook of Optics*, $2^{nd}$ edition, ed. Michael Bass, McGraw-Hill Inc., New York, 1995, pp. 27.1 ff.) Spectroscopic ellipsometery measures such functions over a range of wavelengths, e.g., 240 to 800 nm, and at one or more angles of incidence, e.g, 60, 65 and 70 degrees from normal. For the current application, some range of wavelengths and/or angles is needed to measure the multiple parameters describing the heterogeneous structure. Near-Brewster ellipsometry is generally used to measure film thickness. Near-normal incidence ellipsometry has no sensitivity to thickness of homogeneous films, and so is especially desirable for the present application. Another option is variable-angle reflectometry which collects information about reflected intensity over a range of angles and preferably wavelength. Other suitable data reflected intensity for known directions of incident and reflected polarization, as collect bypolarization dependent reflectometry.

In general, the pitches that are suitable for scalar algorithms like the mixing algorithm are larger than the pitches of device arrays at the critical dimension of modem integrated circuits. The need is to measure the erosion on these arrays. In these cases, a correlation function bridges the gap between the erosion measured on a larger pitch array and the important erosion of device arrays. The correlation function is a mapping from the erosion on one (or more) pitches that have been measured to some pitch of interest. The correlation function is preferably determined empirically by stylus profiles on a range of structures with the pitches in question. Alternatively, the correlation function is determined theoretically based on a physical model of the process, e.g., CMP. The mixing algorithm and related algorithms are useful for additional measurements. In lithography they can be used to measure critical dimension (post exposure, post development, and post etch), degree of development, degree of etching, and quality of etching. They are also suitable to characterize the results of deposition and etch over mesoscale structures. Again a variety of instruments can collect the data, including normal incidence reflectometry, multiple-angle reflectometry, polarization-sensitive reflectometry, and variable angle and/or wavelength ellipsometry.

The use of ultraviolet light (UV) with the mixing algorithm is particularly attractive, especially for small-scale structures. UV has shorter wavelengths than visible light. The mixing algorithm is most applicable where the wavelength of the light is smaller than the lateral dimensions of the heterogeneous structure. Hence UV should be applicable to a wider range of structures. Similarly, infrared light (IR) would be suitable with the mixing algorithm used to interrogate larger structures. For example, dishing is normally an issue for microelectronics manufacture on structures with lateral scales of tens of microns, much greater than the wavelengths of visible light.

Figure 19A:
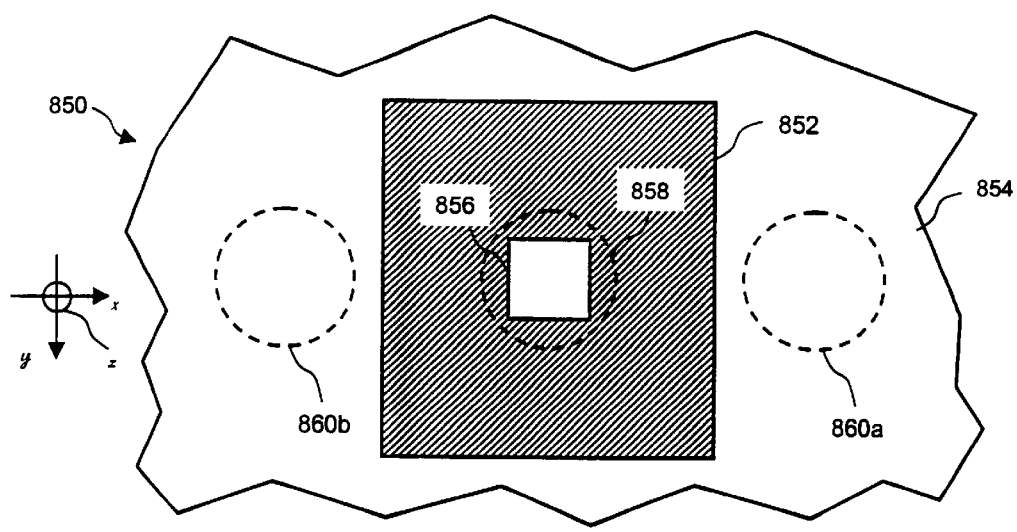
FIG. 19a is a plan view of a collection of spots designed to characterize the dishing of a large metal line with a transparent post.
Figure 19B:
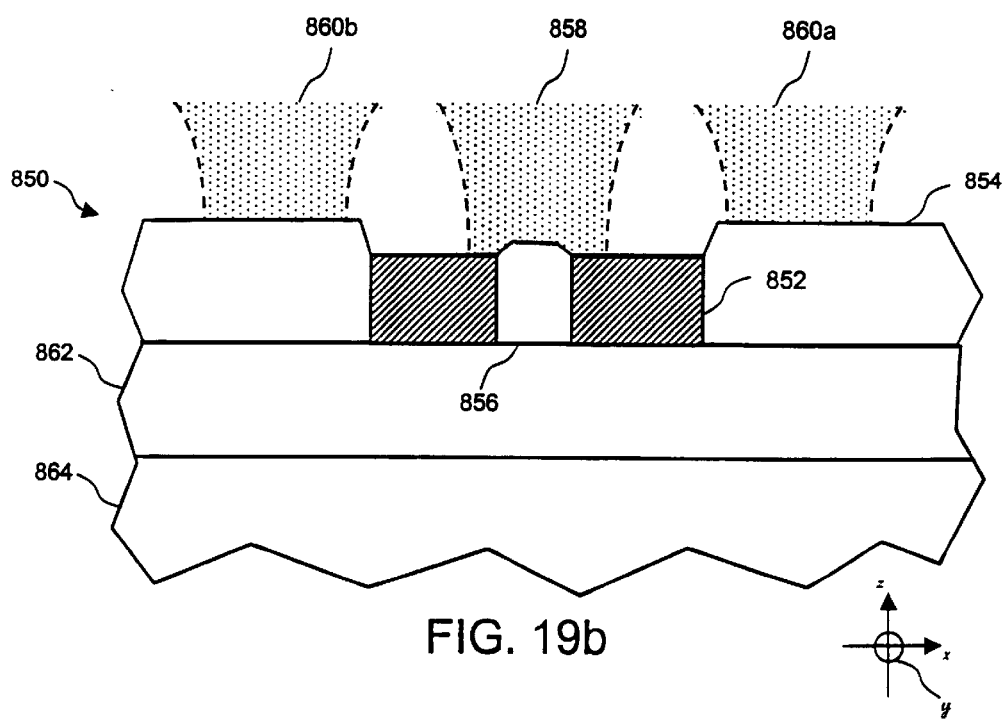

In another aspect of this invention, dishing is measured with a collection of spots, as illustrated in FIGS. 19a and 19b. This approach addresses the problem of measuring dishing on pads or lines that have lateral dimensions of tens of microns after chemical mechanical polishing. In this case, a metal structure 852 is surrounded by a field 854, and has a transparent post 856. Structure 852 is typically a contact pad or post or other structure designed to carry high current. Transparent post 856 is either part of the design (e.g., to help prevent dishing), or is present to aid the metrology. It must be small enough to not severely impact the flow of current in structure 852. Spot 858 views at least some of post 856 and possibly some portion of pad 852. Spot 860a views at least some part of field area 854 (and possible some portion of pad 852). Additional optional spots, such as spot 860b provide additional views of field 854. Sample 850 typically has underlayers 862 and substrate 864.

The appropriate algorithm discussed above (e.g., flow diagram 700), processes data from spots 858 and 860 to measure the thicknesses of post 856 and field 854, respectively. If there are multiple spots 860 over the field, their thicknesses are preferrable averaged, or otherwise combined to yield an effective field thickness in the vicinity of pad 852. The difference between the effective field thickness and the thickness of the post is taken as an indicator of the degree of dishing. As shown in FIG. 19b, post 856 is likely to protrude above the surface of pad 852. Thus, it would generally be appropriate to calibrate the difference between the thicknesses d to the actual dishing D by a smooth function) in order to account empirically for the protrusion:

$$D=F(d).\qquad\text{Eq. 15}$$

Function F is preferably a low-order polynomial, preferably of order one:

$$F(d)=f_0+f_1 d\qquad\text{Eq. 16}$$

or alternatively, by a higher order polynomial:

$$F(d)=f_0+f_1 d+f_2 d^2\qquad\text{Eq. 17}$$

where $f_0, f_1, f_2$, etc. are constants, preferably determined by correlation to results from cross-section scanning-electron micrographs or stylus profiles.

Transparent post 856 preferably is small enough to not severely impact the flow of current in structure 852, and to not suffer from significant protrusion. Underlayers 862 may have three-dimensional structures. Transparent post 856 preferably has a cross sectional area that is a large fraction of the cross-sectional area of spot 858. Transparent post 856 optionally is a collection of posts that fall within spot 858. If post 856 is not typically placed in other structures on the sample like structure 852, the dishing calculated for sample 850 is preferably calibrated for other more typical structures, in the manner described above in conjunction with Equations 15–17.

Figure 20A:
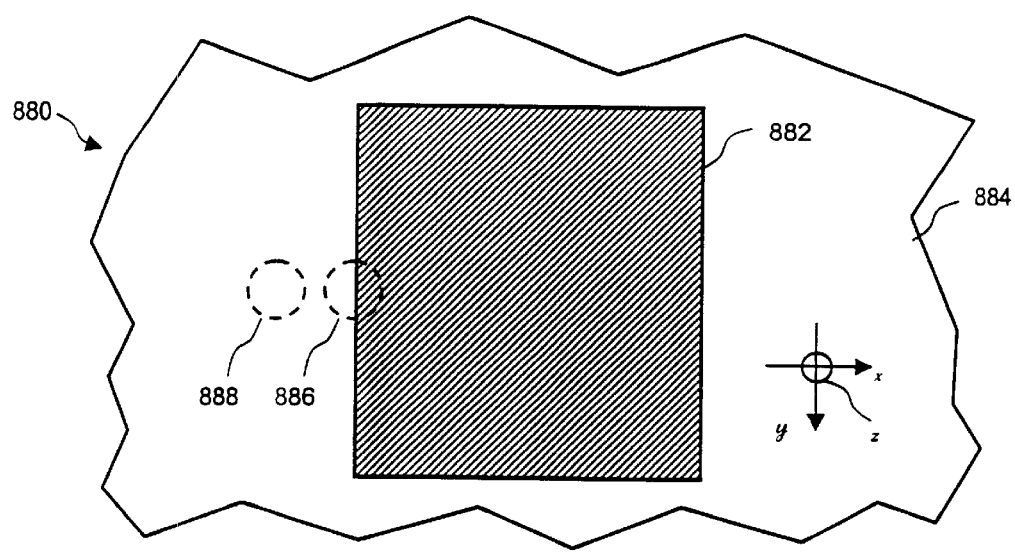
FIG. 20a is a plan view of a collection of measurement spots designed to characterize oxide dishing near a large metal line.
Figure 20B:
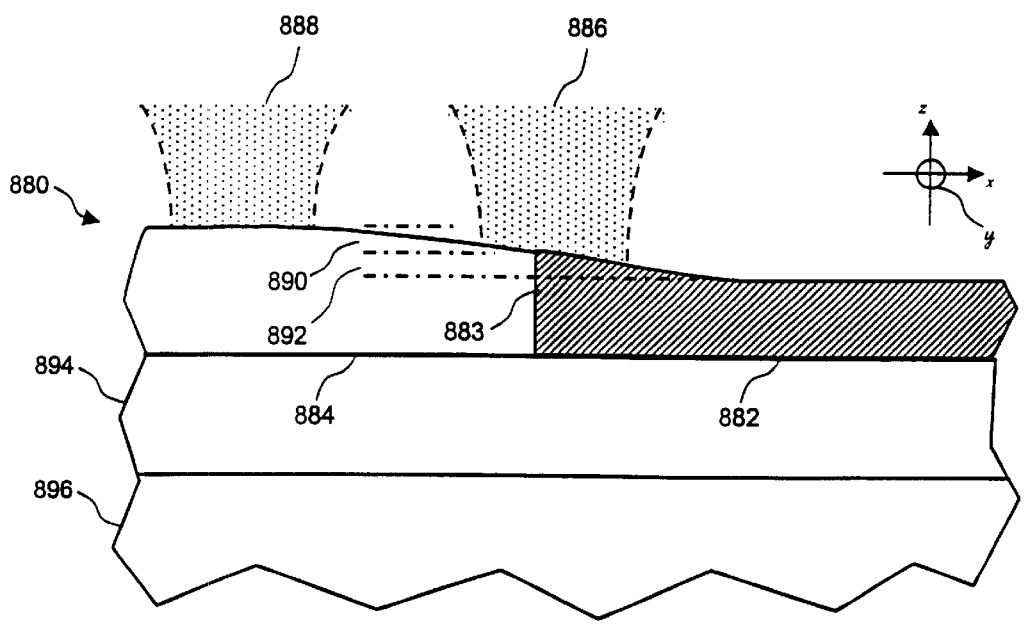

With reference now to FIGS. 20a and 20b, a method for measuring a component of dishing at a sample 880 is now described. Metal structure 882 on sample 880 is surrounded by a field 884. Structure 882 may be a contact pad or post or other structure designed to carry high current. Spot 886 sees at least some of each structure 882 and structure 884, i.e., it lies across boundary 883. Spot 888 lies substantially in a high (thick) portion of field 884. Optionally, several spots are used along either boundary in the field. Sample 880 also comprises underlying structures 894 and substrate 896. Oxide dishing 890 is the difference in level between the field and the boundary between the field and the structure. Metal dishing 892 is the difference in level between the boundary and the center of the structure. Total dishing is the combination of the two.

The appropriate algorithm discussed above (e.g., flow diagram 700 of FIG. 16), processes data from spots 886 and 888 to measure the thicknesses of field 884 at both locations. If there are multiple field or boundary spots, their thicknesses are preferrable averaged, or otherwise combined to yield an effective thicknesses in the field and at the boundary. The difference between the two measured thicknesses, over the field and at the edge, is an indicator of the oxide component of dishing. This difference is generally not be exactly the oxide dishing because it is an average over the portion of the field near the boundary that is sloping up towards the field plateau. This difference is preferably calibrated to the total dishing, as described above in conjunction with Equations. 15–17. Alternatively, this difference can be calibrated to the actual oxide dishing.

Figure 21A:
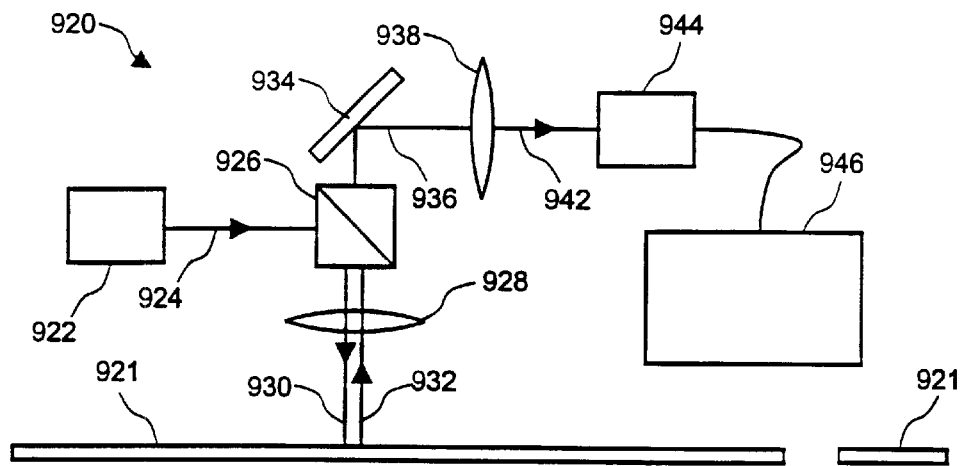
FIG. 21a is an optical measurement apparatus suitable for practicing the present invention for optically measuring at least one parameter of multiple zones on a processed wafer.

A suitable apparatus for measuring intensities reflected from samples for the practice of the above-described methods of the present invention is set forth in aforementioned U.S. patent application Ser. No. 09/533,613. FIG. 21a shows a simplified version of the apparatus described therein. Illuminator 922 emits light 924, which is deflected by beamsplitter 926 towards sample 921. Focusing element 928 focuses light 930 onto the sample, and collimates reflected light 932, which passes back through beamsplitter 926. Turn mirror 934 deflects the collimated light 936 through second focusing element 938.

Figure 7:
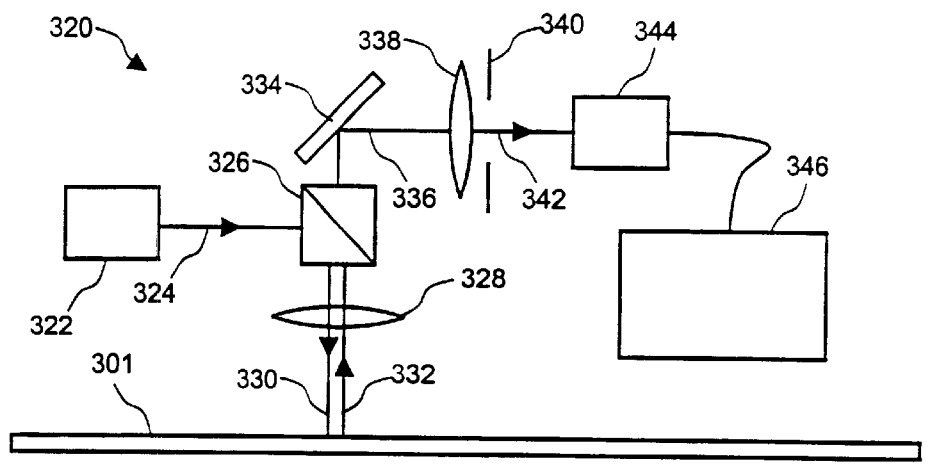
FIG. 7 is a prior art apparatus for optically measuring at least one parameter of an array.

The apparatus of FIG. 21a differs from that of FIG. 7 in that the former lacks aperture stop 340, which blocks high-order diffracted components reflecting from the sample. Processor 946 processes the spectroscopic, specular data from detector system 944 to measure at least one parameter of sample 921. Although not shown, apparatus 920 allows relative motion between the optics, e.g. focusing element 928 and sample 901, and further allows optical system to view reference sample 901. The components of optical system 920 are preferably chosen to allow for operation over the ultraviolet, visible, and near infrared spectra. The system also preferably includes a vision system and pattern-recognition software on processor 946 to allow the system to be trained to make measurements at predetermined locations on samples, and to take advantage of the large-scale repetition of patterns on typical samples, e.g., stepper fields on a silicon wafer for microelectronics manufacture.

Some advantages of the method of the present invention compared to the Finarov technique result from not requiring collection of light that is substantially specular, i.e., because the current method works with substantial non-specular components that must be excluded in the Finarov technique. One of the advantages of the method of the present invention is not having adjustable aperture stop 340 (FIG. 7).

Figure 8:
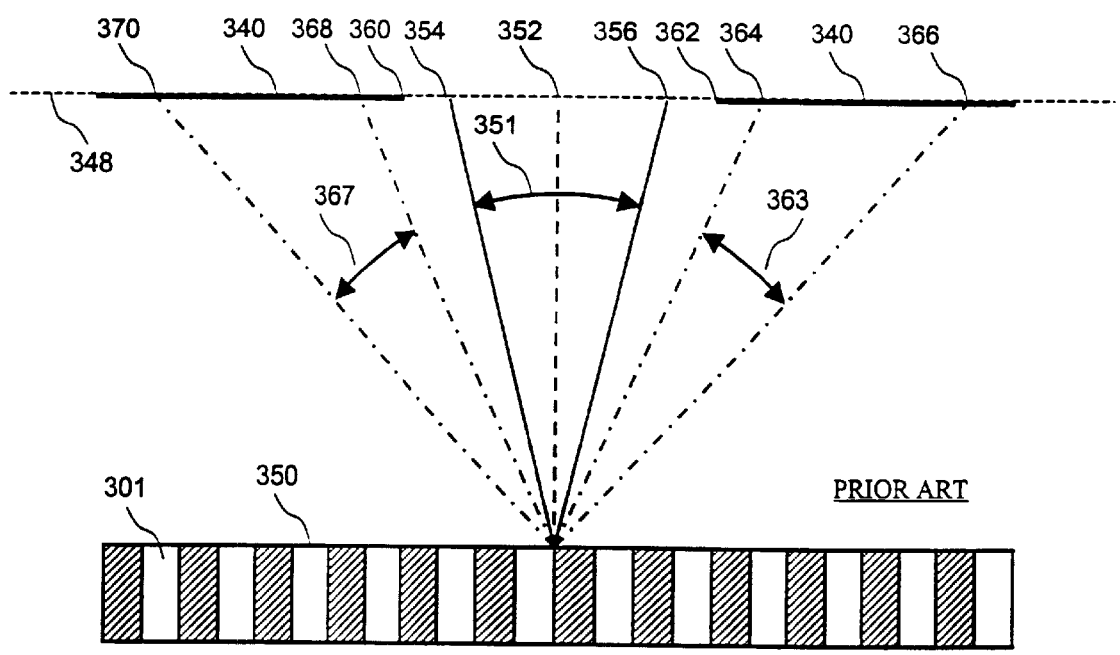
FIG. 8 is a prior art representation of an aperture to block higher order scattered light from an array.
Figure 21B:
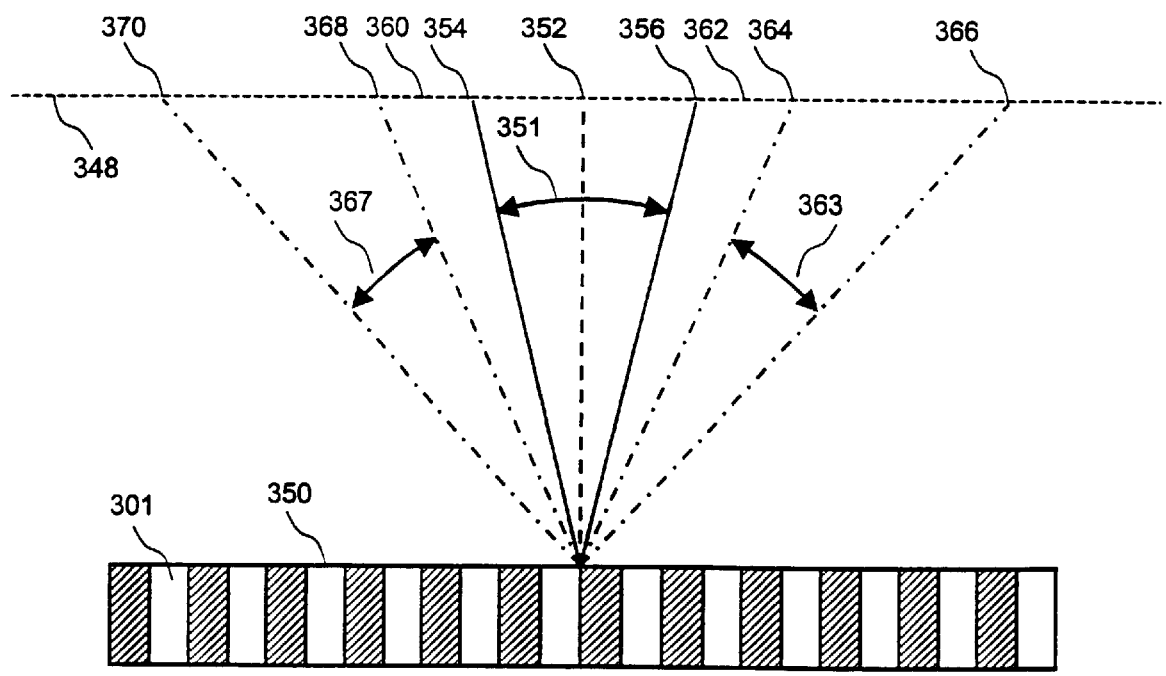
FIG. 21b is a schematic diagram of a grating zone illustrating how multiple orders of diffracted light are collected for use in the present invention.

FIGS. 21*a* and 21*b* show an apparatus suitable for practicing the current invention which is similar to that described for the prior art in connection with FIGS. 7 and 8, but lacks stop 340. Adjustable stop 340 is an additional component that adds complexity to the optical hardware. Further, in order to be practical for use in a manufacturing environment, adjustable stop 340 must be controlled based on the sample location that is being measured. This adds complexity and cost to the mechanics, electronics, control-software, and algorithm recipes. Also, aperture stop 340 blocks certain light from being detected, thereby eliminating a portion of the potential signal. As shown in FIG. 21*b*, with the present invention, higher order scattered light over the ranges 363 and 367 can be detected by the optics to add to the measured intensity and improve the signal-to-noise ratio.

Figure 4:
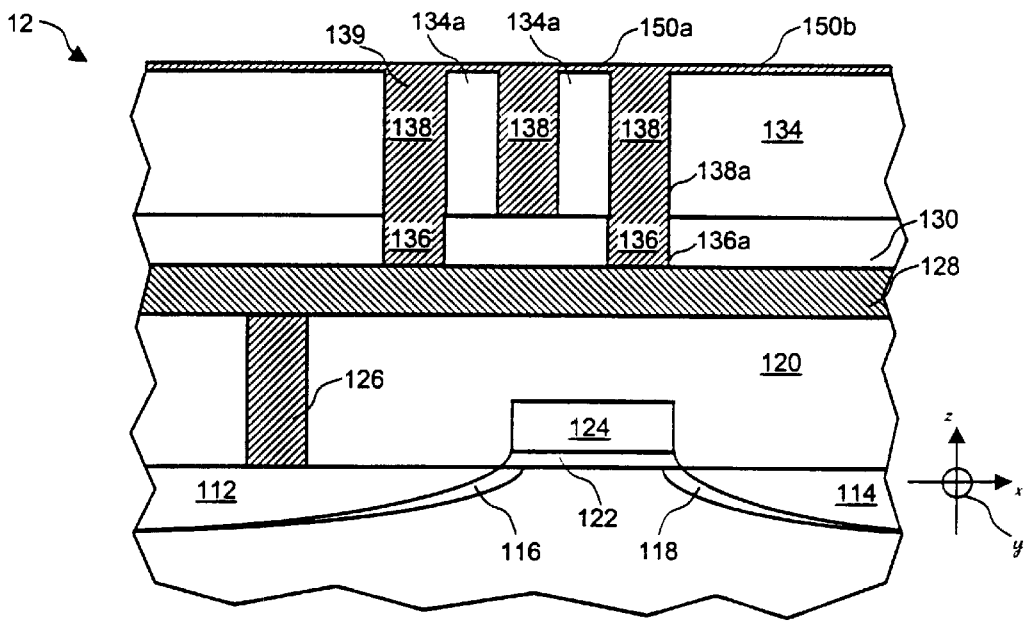
FIG. 4 is the semiconductor structure of FIG. 2 after CMP polish is performed, but with achieving the undesired result of having a portion of the tungsten metal layer remaining as residue atop the semiconductor structure.
Figure 5:
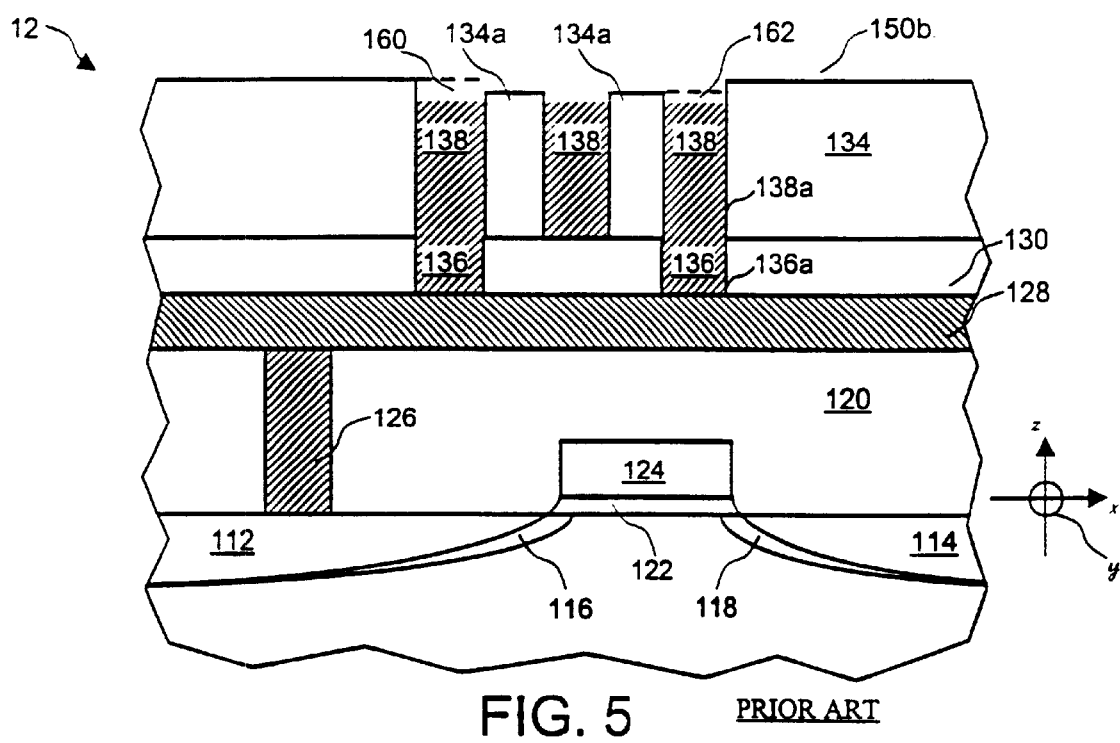
FIG. 5 is the semiconductor structure of FIG. 2 after CMP polish is performed, but with achieving the undesired result of having a erosion of the oxide in the array and dishing of the metal lines in the array.
Figure 22:
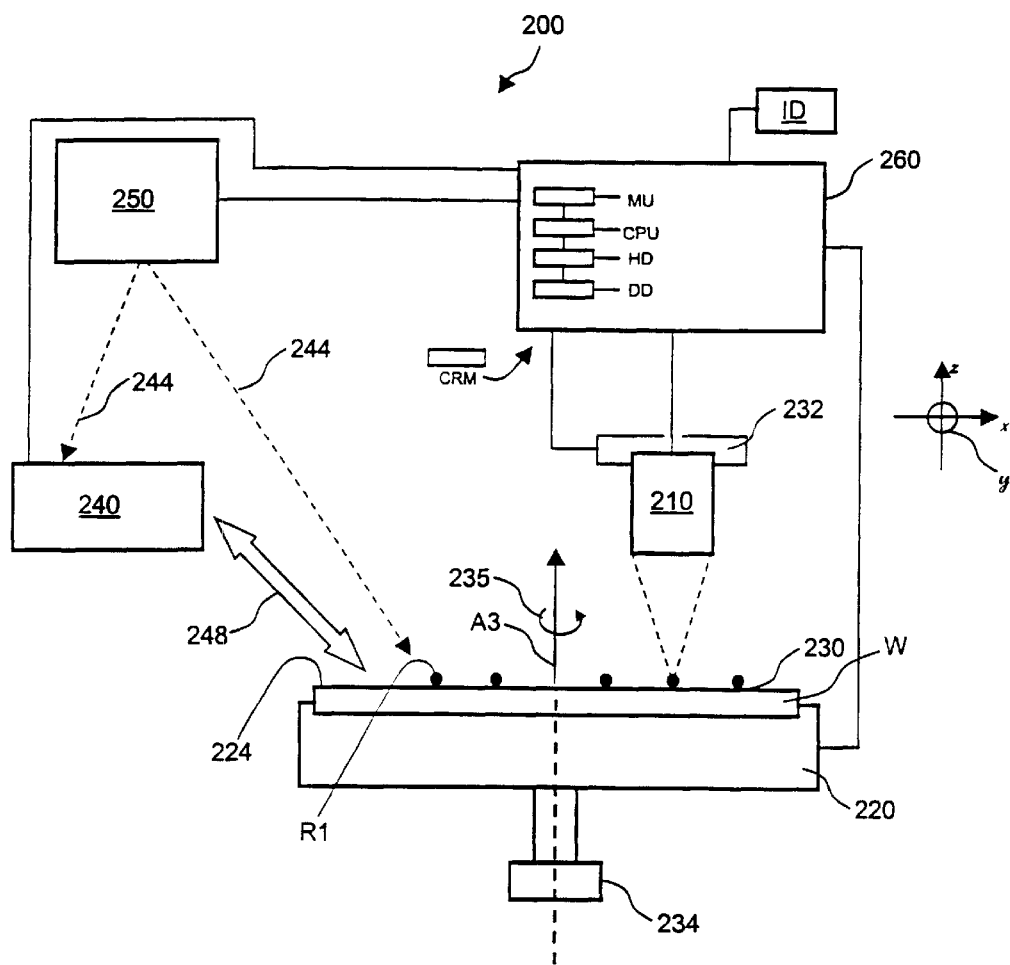
FIG. 22 is a schematic of a system suitable for employing the current invention within the frame work of a process tool with integrated metrology.

With reference now to FIG. 22, there is shown a wafer polishing and measurement system 200 comprising a measurement unit 210 arranged adjacent a wafer stage 220 having an upper surface 224 capable of supporting a wafer W having an upper surface 230. Measurement unit 210 is fixed to a stage 232 capable moving in the X-Y plane in response to an electronic signal. Wafer stage 220 is preferably in operable communication with a drive motor 234 capable of causing rotation of the wafer stage in the X-Y plane about an axis A3 as indicated by arrow 235. Stage 232 is capable of moving wafer W with respect to measurement unit 210 in two dimensions, or vice versa or, move the wafer in one dimension and measurement unit 232 in another. The dimensions of motion could be Cartesian (X and Y) or cylindrical (R and O). In a preferred embodiment, stage 232 as shown in FIG. 4 provides primary motion in a radial direction R parallel to the X direction, and drive motor 234 provides rotary motion measured by angle Φ. Stage 232 also provides auxiliary motion in the Y direction to calibrate the motions. The primary calibration requirement is that the measurement spot of measurement unit 210 on the wafer passes through axis of rotation A3. The orientation of the measurement system with respect to system 200 and to world coordinates (e.g., "up" and "down"), as used above and in the following description, are for illustrative clarity only. For example, system 200 could be inverted or rotated by 90 degrees.

Wafer W is preferably a silicon wafer commonly used in the semiconductor industry for fabricating semiconductor devices. However, though the term "wafer" is used herein for ease of discussion, the method will be understood to apply generally to other types of substrates besides wafers, such as those used for storage-device heads, whereby residue or some other state needs to be detected after processing.

Measurement unit 210 may be a reflectometer assembly for measuring reflectivity (or a related property) of wafer upper surface 230. An exemplary reflectometer assembly is described in U.S. Patent Application Nos. 60/125,462 and 60/128,915, which are incorporated by reference herein. Another exemplary reflectometer is shown in FIG. 21*a*, above. Measurement unit 210 may also be an ellipsometer capable of determining the phase difference Δ between the parallel ($R_p$) and perpendicular ($R_s$) components of a light beam that has been elliptically polarized by reflection from wafer upper surface 230, while at the same time uniquely determining the ellipsometric parameter Ψ of the elliptically polarized beam. Such ellipsometers are described in U.S. Pat. Nos. 4,053,232 and 5,166,752, which patents are incorporated by reference herein. Other suitable measurement units include a polarized reflectometer, such as described in the article by M. E. Lee, C. Galarza, W. Kong, W. Sun, and F. L. Terry, Jr., "Analysis of Reflectometry and Ellipsometry Data from Patterned Structures," International Conference on Characterization and Metrology for ULSI Technology, Gaithersburg, Md., Mar. 23–27, 1998, AIP Conference Proceedings 449, pp. 331–5 (1998), or a beam-profile reflectometer, such as described in U.S. Pat. No. 4,999,014, or any other reflectometer that measures the reflected intensity as a function of angles of incidence and reflection. Furthermore, combinations of such instruments would be suitable measurement units. In the latter case, the reflection properties described above would be combinations of data acquired by the component measurement systems.

Measurement unit 210 is thus described herein as being capable of measuring "reflection properties" from upper surface 230 of wafer W. The term measuring "reflection properties" is used broadly and is meant to include any measurement made on the sample, such as detection of a signal as a function of wavelength that contains ellipsometric information, reflectivity information, or other such information obtainable by sensing reflected light from wafer W. Also, any transform of such properties is also considered as properties in the present invention. This will particularly be the case when these spectra are transformed, possibly with other measured or known information, to calibrate the instrument or to increase the sensitivity of the raw measurements to the parameters of interest, e.g., the erosion.

Figure 1:
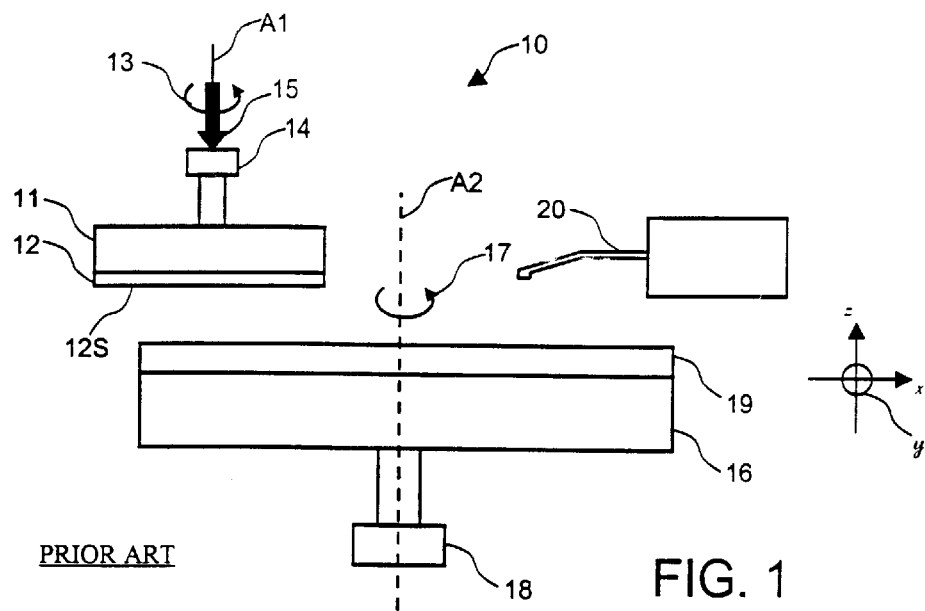
FIG. 1 is a cross-sectional schematic diagram of a prior art CMP apparatus.
Figure 2:
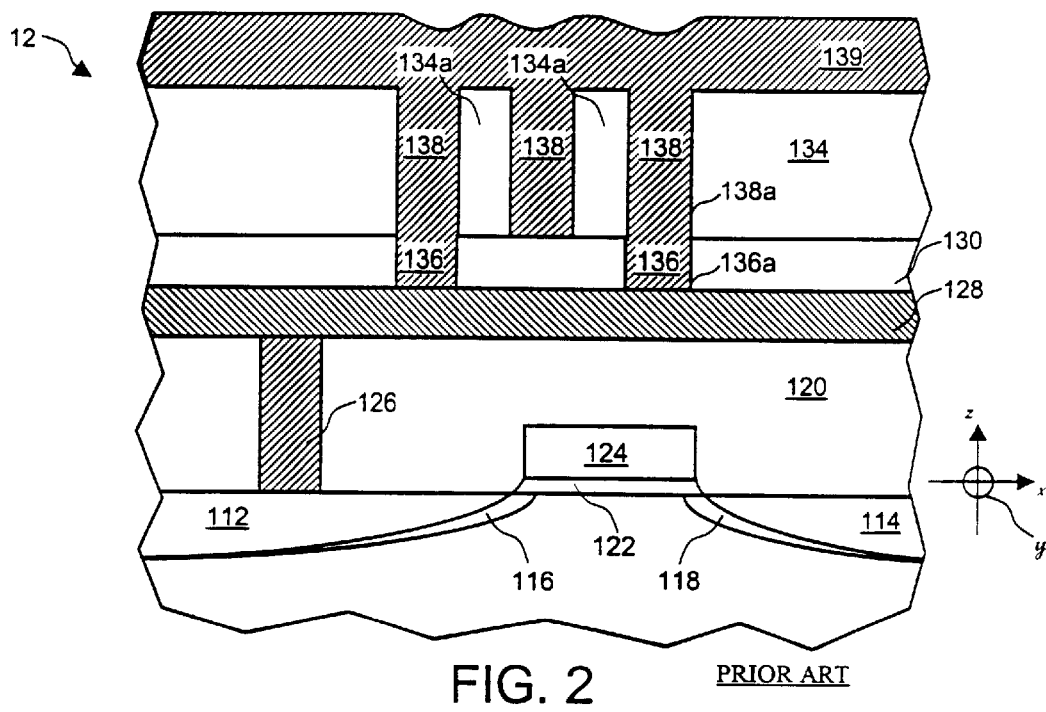
FIG. 2 is a prior art schematic cross-sectional diagram of a section of semiconductor structure in a wafer, illustrating the fabrication by CMP of tungsten contact studs embedded in silicon dioxide, with an upper layer of tungsten present prior to CMP polish.
Figure 3:
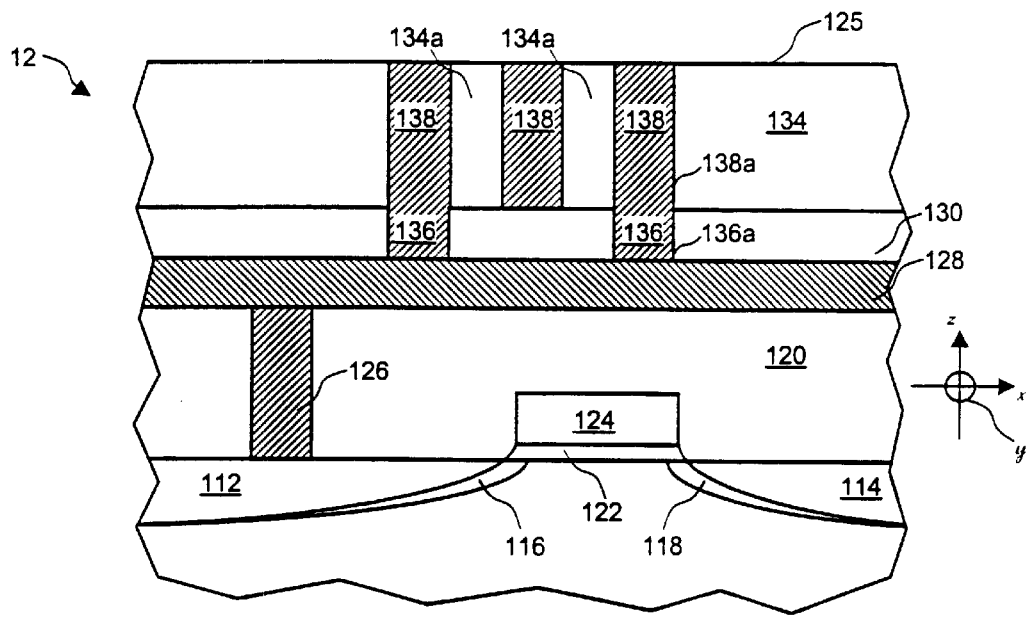
FIG. 3 is the semiconductor structure of FIG. 2 after CMP polish is performed to achieve the desired planarization with the complete removal of the excess tungsten.

With continuing reference to FIG. 22, system 200 further includes a CMP apparatus 240, such as apparatus 10 of FIG. 1, and a wafer handling system 250 in operative communication with the CMP apparatus and wafer stage 220 (as indicated by the dashed arrows 244 and 246) for transferring wafers W between the CMP apparatus and the wafer stage (as indicated by the double arrow 248).

Apparatus 10 also preferably includes a control system 260 electrically connected to wafer handling system 250, CMP apparatus 240, wafer stage 220 and measurement unit 210. In a preferred embodiment, control system 260 is a computer having a memory unit MU with both random-access memory (RAM) and read-only memory (ROM), a central processing unit CPU (e.g., a PENTIUM™ processor from Intel Corporation), and a hard disk HD, all electronically connected. Hard disk HD serves as a secondary computer-readable storage medium, and may be, for example, a hard disk drive for storing information corresponding to instructions for control system 260 to control the devices connected thereto. Control system 260 also preferably includes a disk drive DD, electronically connected to hard disk HD, memory unit MU and central processing unit CPU, wherein the disk drive is capable of accepting and reading (and even writing to) a computer-readable medium CRM, such as a floppy disk or compact disk (CD), on which is stored information corresponding to instructions for control system 260 to carry out the method steps of the present invention. Control system 260 also preferably includes an input device ID for inputting information into the control system. An exemplary control system 260 is a computer, such as a DELL PRECISION WORKSTATION 610™, available from Dell Corporation, Dallas, Tex. Control system 260 is programmed to control the operation of the above-described elements making up system 200 to carry out the methods of the present invention, as described below.

Control system 260, CMP apparatus 240, wafer stage 220 and measurement unit 210 may be operated as an integrated system or in a stand-alone geometry with operable communication therebetween. Control system 260 can be a distributed control system comprised of separate but interconnected computers, e.g., one for the CMP apparatus, one for the measurement unit, etc. Control system 260, wafer stage 220 and measurement unit 210 constitute a residue detection apparatus according to the present invention.

Figure 23:
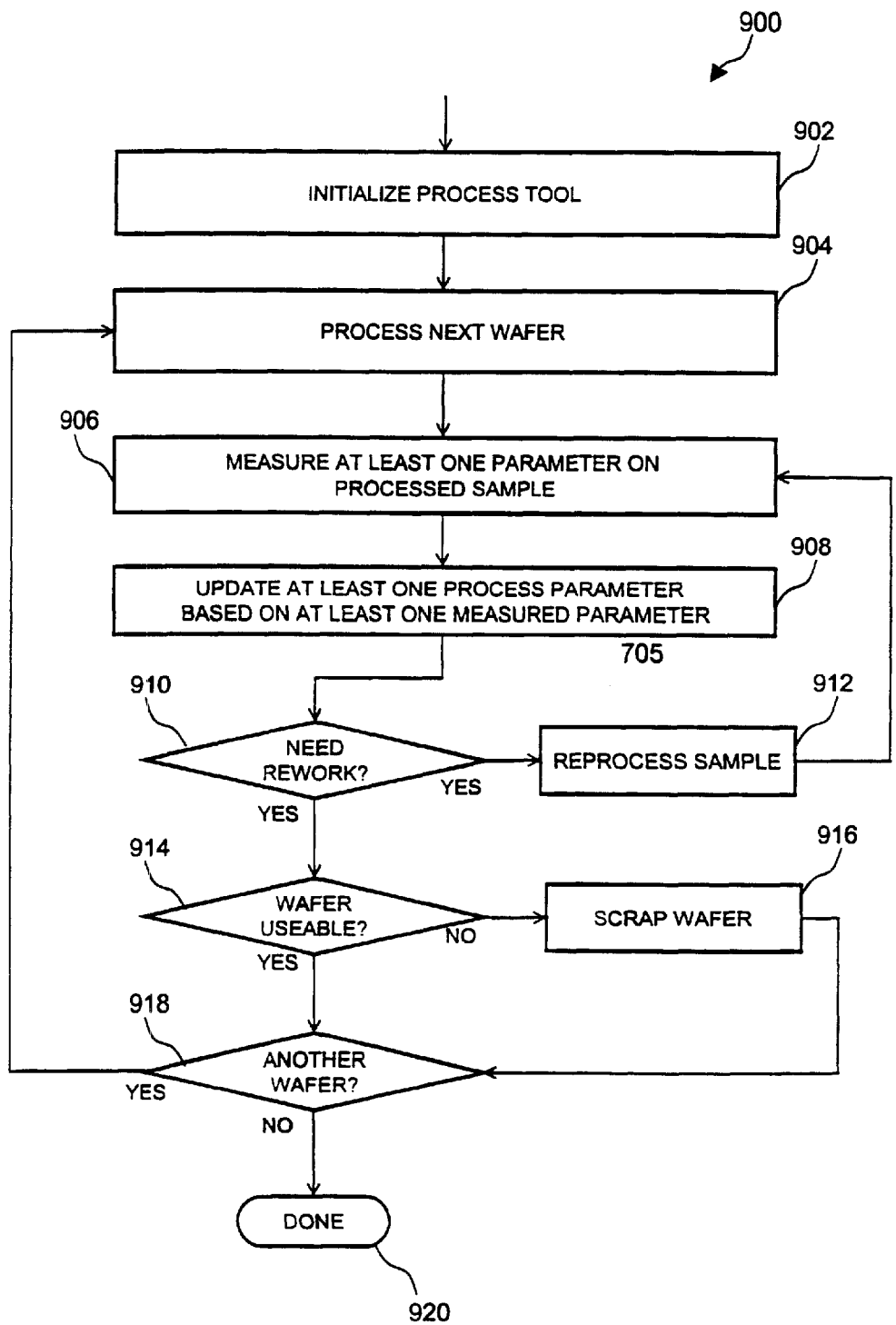
FIG. 23 is a diagram of a control process using the current invention.

FIG. 23 is a flow diagram for using the current method to control a semiconductor process within a process tool like that shown in FIG. 22. The process is preferably CMP, but could be etch, deposition, or any other suitable process. Preparation includes setting the process parameters for the first sample to be processed. The sample is preferably a silicon wafer with microelectronics being built upon it. In step 902 the process tool is initialized, i.e., prepared to polish the first wafer. In step 904, the next wafer is processed. In step 906, at least one parameter of the processed sample is measured, preferably with the chain algorithm, e.g., steps 708 and 710 of process 700, shown in FIG. 16. Alternatively, the measurement is performed with the mixing algorithm, e.g., step 529 of FIG. 14. In step 908, the process controller 260 adjusts at least one parameter based on the measured sample parameter from step 906. In optional step 910, the controller uses the measured parameter to determine if the wafer requires rework. If it does need rework, that the sample is reprocessed in step 912 and returned for measurement by step 906. In optional step 914, the controller uses the measured parameter to determine if the wafer is useable. The wafer is useable if the process is successful and the sample is within specification limits. If the wafer is deemed not useable in step 914, it is scrapped in step 916. In step 918, the tool controller determines if there is another wafer to be processed. If so, then control is returned to step 904 to process the next wafer. Otherwise, the process is concluded with step 920.

Alternatively, process 900 could be applied with a process tool and a separate "stand-alone" metrology tool. In this case, a set of samples, eg, a cassette or lot of wafers, would replace a single sample in the control scheme, some other minor modifications.

The many features and advantages of the present invention are apparent from the detailed specification, and, thus, it is intended by the appended claims to cover all such features and advantages of the described apparatus that follow the true spirit and scope of the invention. Furthermore, since numerous modifications and changes will readily occur to those of skill in the art, it is not desired to limit the invention to the exact construction and operation described herein. Accordingly, other embodiments are within the scope of the appended claims.

What is claimed is:

1. A method of measuring at least one parameter associated with a portion of a sample having formed thereon one or more structures with at least first and second different zones each zone having an associated zone reflectance property, the method comprising the steps of:
   a) illuminating the first and second zones with light;
   b) detecting light reflected from both zones;
   c) detecting light reflected primarily from the first zone;
   d) deriving a zone reflectance property for the first zone from the light detected in step (c); and
   e) fitting a parametric model to the light detected in step (b), wherein said parametric model accounts for an interaction between light reflected from the two zones and the zone reflectance property of the first zone derived in step (d).

2. A method according to claim 1, wherein the zone reflectance property of light includes the reflected intensity of unpolarized light or polarized light.

3. A method according to claim 1, wherein the zone reflectance property of light includes a ratio corresponding to the reflection coefficients for parallel and perpendicularly polarized light.

4. A method according to claim 1, wherein the detecting steps take place while the sample is in a process tool.

5. A method according to claim 1, wherein the measured parameter is used to adjust the processing of a subsequent wafer.

6. A method according to claim 5, where the measured parameter is used to adjust the subsequent processing of a subsequent sample on the subsequent wafer.

7. A method according to claim 1, wherein the at least two zones are aperiodic.

8. A method according to claim 1 where the parametric model accounts for the interaction between light emanating from the two zones in one of an incoherent, coherent, or partially coherent manner.

9. A method according to claim 1 wherein the illuminating light s broad band and the reflected and scattered light is detected as a function of wavelength.

10. A method of measuring at least one parameter associated with a portion of a sample having formed thereon one or more structures with at least first and second different zones each zone having an associated zone reflectance property, the method comprising the steps of:
   a) illuminating the sample with light;
   b) obtaining a first measurement of light reflected from the sample, where the detected light has been reflected from a combination of at least the first and second zones;
   c) obtaining a second measurement of light reflected from the sample, where the detected light has been reflected primarily only from the first zone;
   d) calculating theoretical reflectance data corresponding to the response of a parametric model, where the parametric model mixes the zone reflectance properties of the two zones and wherein a zone reflectance property of the first zone is based on the measurement obtained in step (c);
   e) comparing the resulting theoretical data to the measurement obtained in step (b); and
   f) iteratively modifying the parametric model and recalculating the theoretical reflectance data in order to minimize the differences between the calculated data and the measurement obtained in step (b) to evaluate a parameter of the sample.

11. A method according to claim 9 where the parametric model mixes the zone reflectance properties the two zones in one of an incoherent, coherent, or partially coherent manner.

12. A method according to claim 1 wherein the illuminating light is broad band and the reflected light is detected as a function of wavelength.

* * * * *

UNITED STATES PATENT AND TRADEMARK OFFICE
CERTIFICATE OF CORRECTION

PATENT NO.    : 6,623,991 B2                                       Page 1 of 1
DATED         : September 23, 2003
INVENTOR(S)   : Kenneth C. Johnson and Fred E. Stanke It is certified that error appears in the above-identified patent and that said Letters Patent is hereby corrected as shown below:

<u>Title page,</u>
Delete and insert:
-- [65]   Continuation of application No. 09/735,286, filed Dec. 11, 2000, now
          Pat. No. 6,340,602 --

Signed and Sealed this

Thirtieth Day of December, 2003

JAMES E. ROGAN
*Director of the United States Patent and Trademark Office*